(12) United States Patent
Levin et al.

(10) Patent No.: US 7,558,625 B2
(45) Date of Patent: Jul. 7, 2009

(54) COMBINED MICRO-CHANNEL GENERATION AND IONTOPHORESIS FOR TRANSDERMAL DELIVERY OF PHARMACEUTICAL AGENTS

(75) Inventors: Galit Levin, Nordiya (IL); Amikam Gershonowitz, Modi'in (IL); Meir Stern, Rehovot (IL); Amir Sherman, Gedera (IL)

(73) Assignee: TransPharma Medical Ltd., Lod (IL)

( * ) Notice: Subject to any disclaimer, the term of this patent is extended or adjusted under 35 U.S.C. 154(b) by 83 days.

(21) Appl. No.: 11/749,814

(22) Filed: May 17, 2007

(65) Prior Publication Data
US 2007/0260170 A1 Nov. 8, 2007

Related U.S. Application Data

(63) Continuation of application No. PCT/IL2005/001219, filed on Nov. 17, 2005.

(60) Provisional application No. 60/628,558, filed on Nov. 18, 2004.

(51) Int. Cl.
*A61N 1/30* (2006.01)
(52) U.S. Cl. ........................................ 604/20
(58) Field of Classification Search ............. 604/19–20, 604/21; 514/11; 600/309; 607/96; 606/27, 606/28, 41, 159
See application file for complete search history.

(56) References Cited

U.S. PATENT DOCUMENTS

| | | | |
|---|---|---|---|
| 4,250,878 A | 2/1981 | Jacobsen et al. | 128/207.21 |
| 4,383,529 A | 5/1983 | Webster | 604/20 |
| 4,419,092 A | 12/1983 | Jacobsen et al. | 604/20 |
| 4,474,570 A | 10/1984 | Ariura et al. | 604/20 |
| 4,477,971 A | 10/1984 | Jacobsen et al. | 29/877 |
| 4,747,819 A | 5/1988 | Phipps et al. | 604/20 |
| 5,087,242 A | 2/1992 | Petelenz et al. | 604/20 |
| 5,374,241 A | 12/1994 | Lloyd et al. | 604/20 |
| 5,681,580 A | 10/1997 | Jang et al. | 424/449 |
| 5,730,716 A | 3/1998 | Beck et al. | 604/20 |
| 6,148,232 A | 11/2000 | Avrahami | 604/20 |
| 6,317,629 B1 | 11/2001 | Haak et al. | 604/20 |
| 6,611,706 B2 | 8/2003 | Avrahami | 604/20 |
| 6,708,060 B1 | 3/2004 | Avrahami | 604/20 |
| 6,711,435 B2 | 3/2004 | Avrahami | 604/20 |
| 6,731,977 B2 | 5/2004 | Beck | 604/20 |
| 7,123,957 B2 | 10/2006 | Avrahami | 604/20 |
| 7,133,717 B2 * | 11/2006 | Coston et al. | 604/20 |

FOREIGN PATENT DOCUMENTS

| | | |
|---|---|---|
| WO | WO 2004/039426 A2 | 5/2004 |
| WO | WO 2004/039427 A2 | 5/2004 |
| WO | WO 2004/039428 A2 | 5/2004 |
| WO | WO 2004/112689 A2 | 12/2004 |
| WO | WO 2005/056075 A2 | 6/2005 |
| WO | WO 2005/069736 A2 | 8/2005 |

* cited by examiner

*Primary Examiner*—Manuel A Mendez
(74) *Attorney, Agent, or Firm*—Winston & Strawn LLP

(57) ABSTRACT

The present invention relates to methods of transdermal delivery of pharmaceutical agents. In particular, the present invention relates to a method for transdermal delivery by generating micro-channels on the skin of a subject and delivering iontophoretically a pharmaceutical agent through the micro-channels. The method provides synergistic transdermal delivery of such pharmaceutical agents.

13 Claims, 8 Drawing Sheets

COMBINED MICRO-CHANNEL GENERATION AND IONTOPHORESIS FOR TRANSDERMAL DELIVERY OF PHARMACEUTICAL AGENTS

CROSS-REFERENCE TO RELATED APPLICATIONS

This application is a continuation of International application PCT/IL2005/001219 filed Nov. 17, 2005, and claims the benefit of provisional application 60/628,558 filed Nov. 18, 2004 the entire content of each which is expressly incorporated herein by reference thereto.

FIELD OF THE INVENTION

The present invention relates to methods of transdermal delivery of pharmaceutical agents. Particularly, the present invention relates to methods of transdermal delivery of pharmaceutical agents comprising generating micro-channels in the skin of a subject and iontophoretically delivering a pharmaceutical agent through the micro-channels generated. The combination of micro-channel generation and iontophoresis results in synergistic transdermal delivery of the pharmaceutical agents.

BACKGROUND OF THE INVENTION

The skin is a complex structure that functions as a barrier to ingress of foreign substances into the body. Molecules moving from the environment into and through an intact skin must first penetrate the stratum corneum, which acts as highly resistant lipid barrier to penetration of these molecules into the skin. Significant efforts have been put forth in attempts to overcome the barrier of the stratum corneum in order to deliver topically functional agents into the skin.

Iontophoresis is in wide use in the administration of drugs. It effectively delivers an ionic form of a drug through the skin in the presence of an electrical potential. As iontophoresis avoids the gastrointestinal side effects sometimes associated with orally ingested or parenterally administered drugs and because of its non-invasive nature, iontophoresis is preferable to oral administration or to subcutaneous, intramuscular or intravenous injection.

Typically iontophoresis is performed by placing an electrode containing an ionic drug solution in contact with the skin at a location where the drug is to be transported. A second electrode is placed on the skin near the first electrode, and voltage is applied so as to cause current to pass through the skin, thereby completing the electrical circuit between the electrodes. As current flows, the ionic drug molecules migrate through the skin under the influence of the second electrode. One general class of electrode designs involves the use of a conductive element associated with a compartment or pouch into which a drug solution is introduced. One wall of the pouch typically comprises a permeable barrier, which serves to contain the solution, but permits drug ions to pass there through. Examples of such electrodes can be seen in U.S. Pat. Nos. 4,250,878, 4,419,092, and 4,477,971, among others.

A second class of electrode designs involves the use of a conductive element associated with a gel material for containing ionized drug without the use of a pouch. Examples of such bioelectrodes are found in U.S. Pat. Nos. 4,383,529, 4,474,570, and 4,747,819. Typically, these gel-type electrodes incorporate ionized drug into the gel at the time of manufacture.

A third type of electrode designs generally utilizes a conductive element associated with a hydratable element. The hydratable element is typically formed of a stack of sheets of a dry cross-linked hydrogel such as cross-linked polyethylene oxide (PEO). U.S. Pat. Nos. 6,169,920 and 6,317,629 assigned to Alza disclose iontophoretic drug delivery devices. U.S. Pat. Nos. 5,087,242, 5,374,241, 5,730,716, 6,731,977 assigned to Iomed disclose electrodes and devices for iontophoretic delivery of agents. U.S. Pat. No. 5,681,580 assigned to Samsung Electro-Mechanics Co. discloses a patch-type device for iontophoretic transdermal medication of insulin. A different type of transdermal delivery device is disclosed in U.S. Pat. No. 6,148,232 to Avrahami. The device includes a plurality of electrodes, which are applied at respective points on skin of a subject, and a power source that applies electrical energy between two or more of the electrodes to cause ablation of the stratum corneum, primarily beneath the respective electrodes, and to generate micro-channels. Various techniques for limiting ablation to the stratum corneum are described, including spacing of the electrodes and monitoring the electrical resistance of skin between adjacent electrodes. Sintov et al. (J. Controlled Release 89: 311-320, 2003) and U.S. Pat. Nos. 6,597,946; 6,611,706; 6,708,060; and 6,711,435 to Avrahami disclose improvements and additional devices for ablating the stratum corneum and generating micro-channels so as to facilitate transdermal passage of substances through the skin. The devices are aimed at reducing sensation and minimizing damage to skin underlying the stratum corneum during micro-channel generation.

International PCT Applications Publication Nos. WO 2004/039426; WO 2004/039427WO 2004/039428; WO2004/112689; WO2005/056075 and WO2005/069736, all assigned to the applicant of the present invention, disclose systems and methods for transdermal delivery of pharmaceutical and cosmetic agents. Specifically disclosed are systems and methods for transdermal delivery of hydrophilic anti-emetic agents, dried or lyophilized polypeptide compositions, water-insoluble drugs and polynucleotides.

There is still a recognized need for, and it would be highly advantageous to have, efficient methods for transdermal delivery of pharmaceutical agents generally and polypeptides in particular, which methods provide improved delivery and bioavailability over that of the known methods.

SUMMARY OF THE INVENTION

The present invention provides effective methods for transdermal delivery of pharmaceutical agents comprising generating micro-channels in a region of the skin of a subject and delivering the pharmaceutical agents by iontophoresis at the region of the skin where micro-channels are present.

Unexpectedly, it is now disclosed that methods comprising both the steps of: (i) generating micro-channels on a region of the skin of a subject; and (ii) delivering iontophoretically a pharmaceutical agent through the micro-channels, result in higher bioavailability of the pharmaceutical agent than obtained by administering the pharmaceutical agent, without iontophoresis, to a region of the skin where micro-channels have been generated or by applying iontophoresis to intact skin.

It is further disclosed that methods comprising both the steps of: (i) generating micro-channels on a region of the skin of a subject; and (ii) iontophoretically delivering a pharmaceutical agent through the micro-channels, achieve high blood concentrations of the pharmaceutical agent similar to those obtained by subcutaneous injection.

It is further disclosed that the methods of the present invention involve minimal skin irritation. Thus, the methods of the present inventions are highly advantageous over subcutaneous injection because of their relatively benign and painless nature. The methods of the present invention are also preferable over either iontophoresis or micro-channel generation alone because they achieve higher permeation and bioavailability of the pharmaceutical agents delivered as compared to each of these methods.

According to a first aspect, the present invention provides a method for transdermal delivery of a pharmaceutical agent to a subject, the method comprising the steps:
(a) generating a plurality of micro-channels in a first region of the skin of a subject;
(b) placing a first electrode assembly on the first region of the skin of the subject where the plurality of micro-channels are present, the first electrode assembly comprising a first electrode and an agent reservoir comprising a pharmaceutical agent, the agent reservoir being electrically connected to the first electrode;
(c) placing a second electrode assembly on a second region of the skin of the subject, the second electrode assembly comprising a second electrode and an electrolyte reservoir; and
(d) applying electric energy between a power supply and the first and second electrodes of (b) and (c), said first and second electrodes electrically connected to the power supply, thereby delivering iontophoretically the pharmaceutical agent through said plurality of micro-channels into the skin of the subject.

The term "micro-channel" as used in the context of the present invention refers to a pathway, generally extending from the surface of the skin through all or significant part of the stratum corneum, through which molecules can diffuse.

It is to be understood that the second region of the skin can be on, near, overlapping, adjacent, or distinct from the first region of the skin. The electrode assemblies can likewise be attached, overlapping, adjacent or distinct from one another. In the event that the two electrode assemblies are combined in a single unit it is to be understood that steps (b) and (c) are carried out concomitantly.

According to some embodiments, steps (b-d) of the method of the present invention can be carried out as many times as required so as to achieve therapeutic blood concentrations of said pharmaceutical agent and to improve the clinical status of the subject.

It must be stressed that the two operations, i.e., generation of micro-channels and iontophoresis, are performed sequentially but not necessarily in immediate succession, i.e., so long as the micro-channels are open. According to some embodiments, steps (b-d) are performed within about 24 hours from the time the micro-channels have been generated, preferably steps (b-d) are performed within about 10 hours from the time the micro-channels have been generated, and more preferably steps (b-d) are performed within about 6 hours from the time the micro-channels have been generated.

According to some embodiments, generating a plurality of micro-channels in the skin of a subject is performed by a micro-channel generating apparatus, the micro-channel generating apparatus comprises:
(i) an electrode cartridge comprising a plurality of electrodes; and
(ii) a main unit comprising a control unit which is adapted to apply electrical energy between the plurality of electrodes of (i) when said plurality of electrodes are in vicinity of a first region of the skin, enabling ablation of stratum corneum in the first region of the skin beneath the plurality of electrodes, thereby generating a plurality of micro-channels.

According to some embodiments, the electrodes having a diameter of about 30 to about 150 microns. According to additional embodiments, the electrodes having a diameter of about 40 to 100 microns. According to an exemplary embodiment, the electrodes having a diameter of about 80 microns. According to further embodiments, the electrodes having a length of about 30 to about 500 microns. According to some embodiments, the electrodes having a length of 40 to 150 microns.

According to some embodiments, the control unit of the micro-channel generating apparatus generates current flow or one or more sparks. According to additional embodiments, the control unit of the micro-channel generating apparatus comprises circuitry to control the magnitude, frequency, and/or duration of the electrical energy delivered to the electrodes, so as to control the current flow or spark generation, and thus the width, depth and shape of the plurality of micro-channels. Preferably, the electrical energy applied by the control unit of the micro-channel generating apparatus is of radio frequency.

According to currently preferred embodiments, the electrode cartridge of the micro-channel generating apparatus generates a plurality of micro-channels having uniform shape and dimensions. Preferably, the electrode cartridge is removable. More preferably, the electrode cartridge is discarded after one use, and as such it is designed for easy attachment to the main unit and subsequent detachment from the main unit.

According to some embodiments, the micro-channels generated have a density of about 75 micro-channels/cm$^2$ to about 450 micro-channels/cm$^2$. According to some embodiments, the micro-channels generated have a density of about 75 micro-channels/cm$^2$ to about 300 micro-channels/cm$^2$. According to certain exemplary embodiments, the density of the micro-channels generated is of about 150 micro-channels/cm$^2$.

According to some embodiments, any iontophoretic delivery device known in the art can be used for iontophoretically delivery of the pharmaceutical agent. It is to be understood that the electrical energy applied for iontophoretic delivery is a direct current of low voltage, and as it dissipates on a large surface area of the electrode assembly of the iontophoretic device, the current density is low. In contrast, the electrical energy applied to the electrodes of the micro-channel generating apparatus is of radio frequency at a high voltage, and as it dissipates on a small surface area of the electrodes, the current density is high. Thus, while the electrical energy applied to the electrodes of the micro-channel generating apparatus is capable of producing micro-channels in the skin of a subject, the electrical current applied for iontophoretic delivery cannot produce such micro-channels, but can promote movement of the pharmaceutical agents.

According to some embodiments, the pharmaceutical agent to be delivered by the method of the present invention is selected from the group consisting of anti-infectives such as antibiotics and antiviral agents, analgesics and analgesic combinations, anesthetics, anti-arthritics, anti-asthmatic agents, anticonvulsants, anti-depressants, anti-diabetic agents, anti-diarrhea agents, antihistamines, anti-inflammatory agents, anti-migraine preparations, anti-motion sickness preparations, anti-nauseants, anti-neoplastics, anti-parkinsonism drugs, antipruritics, antipsychotics, antipyretics, antispasmodics including gastrointestinal and urinary, anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral, central nervous system stimulants, cough and cold suppressants, decongestants, diagnostics, hormones, hypnotics, immunosuppressives, muscle relaxants, parasympatholytics, parasympathomimetics, psychostimulants, sedatives and tranquilizers.

According to other embodiments, the pharmaceutical agent is a peptide, polypeptide or protein selected from the group consisting of insulin, proinsulin, follicle stimulating hormone, insulin like growth factor- 1, insulin like growth factor-2, platelet derived growth factor, epidermal growth factor, fibroblast growth factors, nerve growth factor, transforming growth factors, tumor necrosis factor, calcitonin, parathyroid hormone, growth hormone, bone morphogenic protein, erythropoietin, hemopoietic growth factors, luteinizing hormone, calcitonin, glucagons, clotting factors such as factor VIIIC, factor IX, tissue factor, and von Willebrand factor, anti-clotting factors such as Protein C, atrial natriuretic factor, lung surfactant, plasminogen activators such as urokinase and tissue-type plasminogen activator, bombesin, thrombin, enkephalinase, collagen, collagen domain, mullerian-inhibiting agent, relaxin A-chain, relaxin B-chain, pro-relaxin, inhibin, activin, vascular endothelial growth factors, receptors for hormones or growth factors, integrin, protein A, protein D, rheumatoid factors, neurotrophic factors such as bone-derived neurotrophic factor (BDNF), neurotrophin-3, -4, -5, and -6 (NT-3, NT-4, NT-5, and NT-6), CD proteins such as CD-3, CD-4, CD-8, and CD-19, osteoinductive factors, immunotoxins, interferons such as interferon-alpha, -beta, and -gamma, colony stimulating factors (CSFs) such as M-CSF, GM-CSF, and G-CSF, interleukins (ILs) such as IL-I to IL-IO, superoxide dismutase, surface membrane proteins, decay accelerating factor, viral antigens such as a portion of the AIDS envelope, transport proteins, addressins, regulatory proteins, antibodies, analogs, fragments and pharmaceutically acceptable salts thereof.

According to exemplary embodiments, the pharmaceutical agent is a polypeptide selected from the group consisting of human insulin and human growth hormone (hGH).

According to further embodiments, the pharmaceutical agent reservoir further comprises at least one of the components selected from the group consisting of polymeric materials, electrolytes, preservatives, solubilizing agents, absorption promoters and enzyme inhibitors.

These and other embodiments of the present invention will be better understood in relation to the figures, description, examples, and claims that follow.

DETAILED DESCRIPTION OF THE INVENTION

Figure 1:
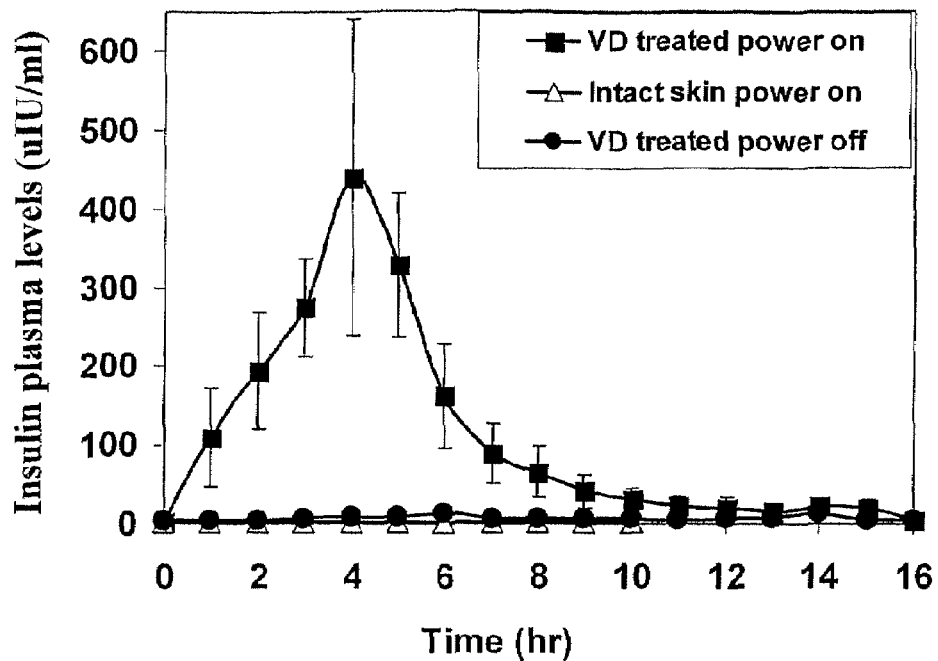
FIG. 1 shows transdermal delivery of insulin to pigs. Insulin was delivered through skin of pigs either by ViaDerm treatment, which generated micro-channels, followed by application of an iontophoretic patch containing insulin when no current was supplied (circles), by application on intact skin of an iontophoretic patch containing insulin when current was supplied (triangles), or by ViaDerm treatment followed by application of an iontophoretic patch containing insulin when current was supplied (squares). Insulin plasma concentrations were measured.

The present invention provides methods for effective transdermal delivery of pharmaceutical agents through skin of a subject.

According to a first aspect, the present invention provides a method for transdermal delivery of a pharmaceutical agent to a subject, the method comprising the steps:

(a) generating a plurality of micro-channels in a first region of the skin of a subject;

(b) placing a first electrode assembly on the first region of the skin of the subject where the plurality of micro-channels are present, the first electrode assembly comprising a first electrode and an agent reservoir comprising a pharmaceutical agent, the agent reservoir being electrically connected to the first electrode;

(c) placing a second electrode assembly on a second region of the skin of the subject, the second electrode assembly comprises a second electrode and an electrolyte reservoir; and (d) applying electric energy between a power supply and the first and second electrodes of (b) and (c), said first and second electrodes electrically connected to the power supply, thereby delivering iontophoretically the pharmaceutical agent through said plurality of micro-channels into the skin of the subject.

The term "transdermal" delivery as used herein refers to the site of delivery of a pharmaceutical agent. Typically, the delivery is intended to the blood circulation. However, the delivery can include intra-epidermal or intradermal delivery, i.e., to the epidermis or to the dermal layers, respectively, beneath the stratum corneum, e.g., dermal melanocytes or dermal sebaceous glands.

The term "micro-channel" as used in the context of the present application refers to a pathway generally extending from the surface of the skin through all or a significant part of the stratum corneum, through which molecules can diffuse.

Unexpectedly, it is now disclosed that higher delivery and bioavailability of a pharmaceutical agent was achieved in skin in which micro-channels were generated and then iontophoresis was applied on the same region where micro-channels were generated than in skin in which only one of these transdermal delivery methods was performed. The principles of the invention are particularly exemplified herein below using large molecules such as human insulin and human growth hormone (hGH). However, it will be understood that the methods of the present invention are applicable to small as well as large molecules as listed herein below.

Generation of micro-channels through the stratum corneum into the epidermis eliminates the need of molecules to pass tortuous intercellular path within or through the stratum corneum in order to get into viable tissues. This has several implications:

The delivery of molecules occurs mainly through the micro-channels.

There is no need to include penetration enhancers in the formulations. Penetration enhancers disrupt the structure of the stratum corneum, and increase the solubility of molecules through the stratum corneum. However, as such they are responsible for undesired side effects like erythema, edema or pruritis. Elimination of penetration enhancers during micro-channel generation improves skin safety and achieves the desired therapeutic effect.

The delivery of molecules is efficient as the molecules reach the hydrophilic environment of viable tissues underneath the stratum corneum.

The present invention integrates the devices and techniques for creating micro-channels by inducing ablation of the stratum corneum as a result of applying electrical current as disclosed in U.S. Pat. Nos. 6,148,232; 6,597,946; 6,611,706; 6,711,435; 6,708,060; and 6,615,079 and Sintov, A. C., et al., J. Controlled Release 89: 311-320, 2003, the contents of which is incorporated by reference as if fully set forth herein.

According to some embodiments, generating a plurality of micro-channels is performed by a micro-channel generating apparatus, the micro-channel generating apparatus comprises:

(i) an electrode cartridge comprising a plurality of electrodes; and (ii) a main unit comprising a control unit which is adapted to apply electrical energy between the plurality of electrodes of (i) when said plurality of electrodes are in vicinity of a first region of the skin, the control unit typically generating current flow or one or more sparks, enabling ablation of stratum corneum in the first region beneath the plurality of electrodes, thereby generating the plurality of micro-channels.

According to some embodiments, the diameter of the electrodes is in the range of 30 to 150 microns. According to additional embodiments, the diameter of the electrodes within an electrode array is in the range of 40 to 100 microns. According to a certain exemplary embodiment, the diameter of the electrodes within an electrode array is of 80 microns. According to other embodiments, the length of the electrodes is in the range of 30 to 500 microns. According to some embodiments, the length of the electrodes is in the range of 40 to 150 microns.

According to additional embodiments, the control unit of the apparatus comprises circuitry to control the magnitude, frequency, and/or duration of the electrical energy delivered to the electrodes, so as to control the current flow or spark generation, and thus the width, depth and shape of the plurality of micro-channels generated. Preferably, the electrical energy applied by the control unit is of radio frequency.

The micro-channels formed by the micro-channel generating apparatus are hydrophilic. According to some embodiments, the micro-channels have a diameter of about 10 to about 100 microns and a depth of about 20 to about 300 microns. Thus, the micro-channels facilitate the diffusion of small and large molecules such as peptides, polypeptides or proteins, through the skin.

According to the principles of the present invention, the electrode cartridge comprises a plurality of electrodes which form an electrode array. The electrode array generates upon application of an electrical energy a plurality of micro-channels within the stratum corneum of the subject's skin. Typically, however, the overall area of micro-channels generated in the stratum corneum is small compared to the total area covered by the electrode array. The term "plurality" of electrodes or of micro-channels refers herein to two or more electrodes or micro-channels, respectively.

According to a further embodiment, the pressure obtained while placing the micro-channel generating apparatus on a subject's skin activates the electrical energy delivered to the electrodes. Such mode of action ensures that the activation of the electrodes occurs only in a close contact with the skin enabling the desired formation of the micro-channels.

The number and dimension of micro-channels can be adjusted to the amount of the pharmaceutical agent desired to be delivered into the skin.

The electrode cartridge is preferably removable. According to certain embodiments, the electrode cartridge is discarded after one use, and as such is designed for easy attachment to the main unit and subsequent detachment from the main unit.

According to the present invention, micro-channels may be formed by the application of current to the skin in order to ablate the stratum corneum by heating the cells. Spark generation, cessation of spark generation, or a specific current level can be used as a form of feedback, which indicates that the desired depth has been reached and current application should be terminated. For these applications, the electrodes are preferably shaped and/or supported in a cartridge that is conducive to facilitate formation of micro-channels in the stratum corneum to the desired depth, but not beyond that depth. Alternatively, the current can be configured so as to form micro-channels in the stratum corneum without the generation of sparks. The resulted micro-channels are uniform in shape and size.

Thus, according to the present invention, the electrodes can be maintained either in contact with the skin, or in vicinity of the skin, up to a distance of about 500 microns therefrom. According to further embodiments, generating micro-channels is performed by applying electrical current having a frequency between about 10 kHz and 4000 kHz, preferably between about 10 kHz and about 500 kHz, and more preferably at about 100 kHz.

According to additional embodiments, generating micro-channels by the micro-channel generating apparatus is performed to achieve micro-channel density of about 50 micro-channels/cm$^2$ to about 400 micro-channels/cm$^2$. According to some embodiments, the micro-channel density ranges from about 75 micro-channels/cm$^2$ to about 200 micro-channels/cm$^2$. According to exemplary embodiments, the micro-channel density is of about 150 micro-channels/cm$^2$.

According to an exemplary embodiment, the micro-channel generating apparatus referred herein below as ViaDerm contains the following components:

1. A disposable electrode cartridge comprising an array of microelectrodes attached onto the distal end of the main unit.
2. A reusable main unit comprising a control unit, which generates an RF electrical current.

The method of the present invention comprises a step of delivering iontophoretically a pharmaceutical agent. Any known iontophoretic delivery device can be used for delivering a pharmaceutical agent in accordance with the present invention, for example, U.S. Pat. Nos. 4,250,878; 4,383,529; 4,419,092; 4,477,971; 4,474,570; 4,744,787; 4,747,819; 5,087,242; 5,135,477; 5,374,241; 5,415,628; 5,558,632; 5,681,580; 5,730,716; 5,846,217; 6,169,920; 6,317,629; 6,629,968; 6,643,544; 6,731,977; and 6,775,569, incorporated by reference as if fully set forth herein.

Typically, iontophoretic delivery devices include a first electrode assembly or iontophoretic patch, the first electrode assembly or iontophoretic patch includes an active or donor electrode and an agent reservoir containing a pharmaceutical agent to be iontophoretically delivered. The first electrode assembly or patch, in particular the agent reservoir, is adapted to be placed in agent transmitting relation to the skin of the subject. The terms "electrode assembly" and "iontophoretic patch" are used interchangeably throughout the specification and claims and refer to the active or donor electrode and the pharmaceutical agent reservoir. The device also includes a second or counter electrode assembly, which includes an electrolyte reservoir, adapted to be placed in electrical contact with the skin at a location which is adjacent, near or spaced apart from the iontophoretic patch. Further, the device includes an electric power source. The electrodes and the power source are electrically connected and form a closed circuit when the electrode assemblies are placed in current conducting relation to the skin of the subject.

It is to be understood that the first and second electrode assemblies can be adjacent or attached to each other and thus the second electrode assembly is placed adjacent to the first electrode assembly, rather than spaced apart from it.

The donor or active electrode conveys electrical current into the agent reservoir for the delivery of a pharmaceutical agent. The pharmaceutical agent can be ionized or ionizable pharmaceutical agent or can be an agent devoid of electrical charge. The donor electrode is constructed of any of a large variety of electrically conductive materials including both inert and sacrificial or electrochemical materials.

Inert conductive materials are those electrically conductive materials which, when employed in the iontophoretic devices of the invention, do not themselves undergo or participate in electrochemical reactions. Thus, an inert material distributes without being eroded or depleted due to the distribution of current, and conducts current through generating ions by either reduction or oxidation of water. Inert conductive materials typically include, for example, stainless steel, platinum, gold, and carbon or graphite.

Alternatively, the donor electrode can be constructed from a sacrificial conductive material. A material can be considered sacrificial if, when employed as an electrode in an iontophoretic device, the material is eroded or depleted due to its oxidation or reduction. Such erosion or depletion occurs when the materials and formulations used in the iontophoretic device enable a specific electrochemical reaction, such as when a silver electrode is used with a formulation containing chloride ions. In this situation, the electrode would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes can also be employed. In such cases, the metal is oxidized to metal ions, which would then be precipitated as an insoluble salt.

For cathodes, the electrode may be constructed from any electrically conductive material provided an appropriate electrolyte formulation is provided. For example, the cathodic electrode may be constructed from a metal/metal salt material. A preferred cathodic material is a silver/silver halide material. In such embodiments, a metal halide salt is preferably employed as the electrolyte. In other embodiments, the cathodic material may be an intercalation material, an amalgam, or other material, which can take electrolyte cations such as sodium out of solution, below the reduction potential of water. Thus, metals such as silver, copper, zinc, and nickel, and other materials, such as carbon, may be employed when an appropriate metal salt such as silver nitrate or zinc sulfate is in solution in the electrolyte reservoir.

Typically, the agent reservoir contains a pharmaceutical agent to be delivered and the counter reservoir contains a suitable electrolyte. Alternatively, the iontophoretic device can contain a pharmaceutical agent in each reservoir and in that manner both electrode assemblies would function as donor electrode assemblies. For example, positive pharmaceutical agent ions could be delivered through the skin from the anode electrode assembly, while negative pharmaceutical agent ions could be introduced from the cathode electrode assembly.

Typically in iontophoretic devices, an electrolyte reservoir is arranged in electrical communication with a donor or active electrode. The electrical contact requires that electrons from the donor or active electrode are exchanged with ions in the electrolyte reservoir upon the application of electrical current.

The electrolyte reservoir comprises at least one electrolyte, i.e., an ionic or ionizable component, which can act to conduct current toward or away from the donor or active electrode. Typically, the electrolyte comprises one or more mobile ions, the selection of which is dependent upon the desired application. Examples of suitable electrolytes include aqueous solutions of salts such as NaCl. Other electrolytes include salts of physiological ions including, but not limited to, potassium, ($K^+$), chloride ($Cl^-$), and phosphate ($PO_4^-$). The salt and its concentration can be selected as desired for particular applications. Other components can be added to the electrolyte reservoir including, but not limited to, chelation agents, surfactants (e.g., non-ionic, cationic, or anionic), buffers, ionic excipients, osmolarity adjusters, preservatives, enzyme inhibitors, and the like.

Alternatively, the electrolyte reservoir can contain counter ions that form a soluble salt with an electrochemically-generated ion. For example, in a device employing a silver anode, a suitable counter ion might be acetate or nitrate. Such counter ions are useful when other means are provided for sequestering electrochemically generated ions.

Thus, the electrolyte reservoir can provide at least one ion of the same charge as the electrochemically generated ion, to permit current to be conducted, and at least one oppositely charged ion.

The agent reservoir comprising a pharmaceutical agent must be in ionic communication with the skin and in electrical contact with the donor or active electrode. The structure of the agent reservoir may vary depending upon the desired application. The agent reservoir can include a liquid, semi-liquid, semi-solid, or solid material.

According to some embodiments, the agent reservoir includes a solid or semi-solid material such as a gel or other polymeric material. Iontophoresis gels can be karaya gum, other polysaccharide gels, or similar hydrophilic aqueous gels capable of carrying ions. Specific examples of such gels include polyvinyl alcohol, polymethyl pyrollidine methyl cellulose, polyacrylamide, polyhemia, polyhemia derivatives, and the like. The matrix selected should have non-irritating properties to avoid irritating the subject's skin, suitable conductivity properties to obtain good electrical contact with the skin, and the ability to act as a carrier medium for the pharmaceutical agent. The agent reservoir can include a polymeric film in which the pharmaceutical agent to be iontophoretically delivered is dispersed. The mobility of the agent to be delivered is substantially increased by the application of the electric current, permitting effective delivery across the target skin. It can be desirable to provide the solution of the pharmaceutical agent with a buffer. The ion of the buffer of like charge to the agent ion should have low ionic mobility.

A pharmaceutical agent can be delivered from either the anode, the cathode, or both simultaneously. For example, if the pharmaceutical agent to be driven into the body is positively charged, then the positive electrode or anode will be the active electrode and the negative electrode or cathode will serve to complete the electrochemical circuit. Alternatively, if the pharmaceutical agent to be delivered is negatively charged, then the negative electrode will be the active electrode and the positive electrode will be the counter or indifferent electrode.

For iontophoresis, an electric energy is applied to the iontophoretic electrode pair (the active electrode or donor electrode and the counter electrode) from a power supply. The duration of the electric energy applied can vary from about 30 minutes to about 20 hours. However, the electric energy can be applied for shorter or longer periods of time so as to achieve sufficient delivery to yield a therapeutically effective concentration of a pharmaceutical agent. A suitable current density for administering a therapeutically effective dose of a pharmaceutical agent can range from about 0.01 to about 0.5 $mA/cm^2$ though lower or higher current densities are also encompassed in the present invention.

Insoluble or poorly soluble pharmaceutical agents devoid of electrical charge can be mobilized by an electro-osmosis process. Electro-osmosis is a principal mechanism to transport uncharged and/or high molecular weight molecules into the skin by ionic fluxes via the electrode reactions in the iontophoresis process.

The agent reservoir can also include a suitable backing film positioned on top of the agent reservoir. The backing film provides protection against contamination and damage to the reservoir.

The agent reservoir optionally includes a release liner, which can be fixed to the underside of the agent reservoir by an adhesive. The release liner protects the surface of the agent reservoir, which contacts the skin, from contamination and damage when the device is not in use. When the device is ready for use, the release liner may be peeled off to expose the skin-contacting surface of the agent reservoir for application of the device to a subject.

Iontophoretic devices require at least two electrodes to provide a potential to drive an agent into the skin of a subject. Both electrodes are disposed to be in intimate electrical contact with the skin thereby completing the electrochemical circuit formed by the anode and cathode of the iontophoretic device. The anode and cathode can be further defined as an active electrode from which an agent is delivered into the body. An indifferent or counter electrode serves to complete the electrochemical circuit. Various types of counter electrodes may be employed such as, for example, Karaya gel electrode, electrodes described herein above, or as known in the art.

Generally, the combined skin-contacting area of electrode assemblies can range from about 1 $cm^2$ to greater than 200 $cm^2$, but typically ranges from about 1 to 50 $cm^2$.

The pharmaceutical agent to be transdermally delivered according to the present invention can be any pharmaceutical agent which is delivered to a subject to produce a desired, usually beneficial, effect. The pharmaceutical agents that can be delivered by the methods of the present invention include, but are not limited to, anti-infectives such as antibiotics and antiviral agents, analgesics and analgesic combinations, anesthetics, anti-arthritics, anti-asthmatic agents, anticonvulsants, anti-depressants, anti-diabetic agents, anti-diarrhea agents, antihistamines, anti-inflammatory agents, anti-migraine preparations, anti-motion sickness preparations, anti-nauseants, anti-neoplasties, anti-parkinsonism drugs, antipruritics, antipsychotics, antipyretics, antispasmodics, including gastrointestinal and urinary, anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral, central nervous system stimulants, cough and cold suppressants, decongestants, diagnostics, hormones, hypnotics, immunosuppressives, muscle relaxants, parasympatholytics, parasympathomimetics, psychostimulants, sedatives and tranquilizers. Antisense DNA and polynucleotides can also be delivered according to the principles of the present invention.

According to some embodiments, the invention is useful in the transdermal delivery of peptides, polypeptides and proteins including, but not limited to, cardiovascular-active peptides and proteins such as angiotensin II antagonist, bradykinin, and tissue plasminogen activator; CNS-active peptides and proteins such as cholecystokinin (CCK-8 or CCK-32), delta sleep-inducing peptide (DSIP), β-endorphin, melanocyte inhibiting factor-I, melanocyte stimulating hormone, neuropeptide Y and nerve growth factor; GI-active peptides and proteins such as gastrin antagonist, neurotensin, pancreatic enzymes, somatostatin and its analogs such as octreotide; immunomodulating peptides and proteins such as colony stimulating factors, cyclosporine, enkephalins, interferons, muramyl dipeptide, thymopoietin, and tumor necrosis factor; metabolism-modulating peptides and proteins such as growth hormone, gonadotropins, insulin, calcitonin and its analogs such as elcatonin, luteinizing hormone-releasing hormone (LHRH), oxytocin, thyrotropin releasing hormone (TRH), calcitonin gene-related factor, and vasopressins; polypeptide growth factors such as epidermal growth factor (EGF), insulin-like growth factors I and II (IGF-I and II), interleukin-2 (IL-2), nerve growth factor (NGF), platelet-derived growth factor (PDGF), transforming growth factor (TGF), cartilage-derived growth factor, colony stimulating factors (CSFs), endothelial-cell growth factors (ECGFs), erythropoietin, fibroblast-derived growth factor (FDGF), fibroblast growth factors (FGFs), glial growth factor (GGF) and parathyroid hormone (PTH), analogs, derivatives, fragments and pharmaceutical salts thereof.

A "peptide" refers to a polymer in which the monomers are amino acids linked together through amide bonds. "Peptides" are generally smaller than polypeptides, typically under 30-50 amino acids in total.

A "polypeptide" refers to a single polymer of amino acids, generally over 50 amino acids.

A "protein" as used herein refers two or more polymers of amino acids, typically over 50 amino acids each, linked together through amide bonds. Pro-drug forms of naturally occurring peptides, polypeptides and proteins, analogs, derivatives and fragments thereof are also contemplated.

The term "fragment" as used herein refers to a peptide or polypeptide comprising only a portion of a full-length naturally occurring protein.

The term "analog" as used herein refers to peptides, polypeptides or proteins comprising altered sequences by amino acid substitutions, additions, deletions, or chemical modifications.

By using "amino acid substitutions", it is meant that conservative amino acid substitutions and/or non-conservative amino acid substitutions as known in the art can be made within the peptide, polypeptide or protein so long as the peptide, polypeptide or protein retains the biological activity of the naturally occurring molecule. For example, one or more amino acid residues within a naturally occurring peptide, polypeptide or protein can be substituted by another amino acid of a similar polarity, which acts as a functional equivalent, resulting in a silent alteration. Substitutes for an amino acid within a protein may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Chemical modifications of amino acid residues include, but are not limited to, glycosylation, oxidation, permanent phosphorylation, reduction, myristylation, sulfation, acylation, acetylation, ADP-ribosylation, amidation, cyclization, disulfide bond formation, hydroxylation, iodination, methylation, derivatization by protecting/blocking groups, or any other derivatization method known in the art.

Included within the scope of the invention are chimeric or fusion proteins comprising a naturally occurring peptide, polypeptide or protein, a fragment or analog thereof joined at its amino or carboxy-terminus or at one of the side chains via a peptide bond to an amino acid sequence of a different protein.

The pharmaceutical agents of the invention can be formulated as salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The term "pharmaceutically acceptable" means approved by a regulatory agency of the Federal or a state government or listed in the U. S. Pharmacopeia or other generally recognized pharmacopeia for use in animals, and more particularly in humans.

According to the present invention, the pharmaceutical agents must be dissolved in pharmaceutically acceptable carriers, such as water, acetate buffer, phosphate buffer, citrate buffer, carbonate buffer and the like, so as to be administered to the subject. The agent reservoir can comprise an electrolyte for imparting conductivity, pH regulation, buffering and/or skin-protection effect. Other components that can be included in the agent reservoir include, but are not limited to, surfactants, solubilizing agents, preservatives, ion exchange resins, thickeners, emulsifiers, absorption promoters, antibacterial agents, antioxidants, chelating agents and enzyme inhibitors as known in the art. It is to be understood that when the pharmaceutical agent is chemically unstable, the agent can be kept dried in the agent reservoir and then activated by a pharmaceutical acceptable carrier before use.

In accordance with the invention, the pharmaceutical agent is delivered topically, e.g., through the stratum corneum in a region of skin in which micro-channels are present, in a "therapeutic" amount. The term "therapeutic" amount refers to an amount effective to produce a desired effect, such as ameliorating or treating a disease or disorder in a subject in need thereof. The amount required for therapeutic treatment will vary from subject to subject, depending on the gender, age, general condition of the subject, the severity of the condition being treated, the type of formulation, and other factors known in the art.

According to the invention, the pharmaceutical agent is iontophoretically delivered to a region where micro-channels are present. However, the method for administering a pharmaceutical agent to a subject can optionally further comprise additional steps that can increase the efficiency of topically introducing the agent into the skin. The steps can include mechanical or physical action or any composition that increases the permeation of the pharmaceutical agent of the invention.

According to the invention, the iontophoretic delivery of the pharmaceutical agent is performed on the region of skin where micro-channels have been generated reasonably close together in time. Preferably, the iontophoretic delivery is performed immediately after the generation of micro-channels. However, it is to be understood that iontophoretic delivery of a pharmaceutical agent can take place as many times as required as long as the micro-channels remain open, i.e., iontophoretic delivery of a pharmaceutical agent can be performed within about 24 hours from the time the micro-channels being generated, preferably within about 10 hours from the time the micro-channels being generated, and more preferably within 6 hours from the time the micro-channels being generated.

Having now generally described the invention, the same will be more readily understood through reference to the following examples, which are provided by way of illustration and are not intended to be limiting of the present invention.

EXAMPLES

The ViaDerm™ technology (see Sintov et al, J. Controlled Release 89: 311-320, 2003) utilized electrical current of radio frequency (RF) to create RF-MicroChannels™ through the outer layer of the skin. These micro-channels having precise dimensions enabled controlled passage of molecules through and into the skin.

Instruments and Materials

In order to create micro-channels in porcine skin, ViaDerm technology was used (see Sintov et al., J. Controlled Release 89: 311-320, 2003).

In brief, ViaDerm contained the following components:
1. A disposable electrode cartridge comprising an array of microelectrodes attached onto the end of the main unit.
2. A reusable main unit comprising a control unit, which generates an RF electrical current.

Example 1

Transdermal Delivery of Insulin by ViaDerm and Iontophoresis

Instruments and Materials

The ViaDerm device containing electrode array at a density of 75 electrodes/cm² was used in this experiment. The device was applied twice on each location, so that the density of the micro channels was 150/cm². The diameter of each electrode of the electrode array was 80 μm. The skin was treated with an applied voltage of 290V, frequency of 100 kHz, one burst, 9 msec burst length, 25 msec additional time between electrodes, no current limitation, and 1.6 Kg spring. Eight sites were used for the application with a total area of 11.2 cm².

Iontophoresis patches (i.e., electrode assembly) were obtained from Iomed (Trans Q1®, Iomed, USA). A power supply was used to deliver electric energy to the patches. Iontophoresis application parameters were as follows: current density 0.18 mA/cm² sponge (total 1.4 mA), current elevation time (from 0-max) 20 seconds, and current application time 1.5 hours. Three patches were sequentially applied, each one for 1.5 hr. At the end of 4.5 hrs of iontophoresis treatment, the power supply was turned off, and the last patch was left on the skin site.

Human recombinant insulin analog Humalog® (Lispro-100 IU/ml) was purchased from Lilly (Lilly France S.A., Fegershein, France).

Saline infusion bags, 50% w/v dextrose ampoules (20 ml), and 5% w/v dextrose infusion bags were purchased from Teva-Medical (Teva-Medical, Israel). Infusion pump (Infutec 500®, Infutec 2000 Medical systems, Lod, Israel) and fluid administration biorette (20 drops/ml, Plasti-Medical S.p.a, Villamaranza, Italy) were used.

Glucometer® and blood glucose test strips were used (Ascensia Elite, Bayer).

Experimental Procedure

Large white male pigs (10-15 kg each) were deprived from food 24 hr prior the experiment. Anesthesia was performed with Ketamine (10-20 mg/kg) and Xylazine 10% (2-4 mg/Kg) and was maintained with halothane. Blood samples were withdrawn from preinserted two jugular cannulas: one was used for dextrose infusion and the other for blood glucose and insulin level testing.

Blood glucose was measured immediately after cannulation and every 5-15 minutes. Glucose levels were maintained around 40-50 mg/dL by infusion of 20% dextrose solution. Blood samples for insulin analysis were collected every hour for 10-16 hrs. The levels of insulin in plasma were analyzed using ELISA kit (Isoinsulin ELISA 10-1128-01, Mercodia, Uppsala, Sweden). Areas under the concentration curves (AUCs) were calculated using a trapezoid method. The dose efficiency was calculated relatively to the SC values according to the following formula:

$$(AUC_{group}/Dose_{group})/(AUC_{sc}/Dose_{sc}) \times 100 = \text{Dose efficiency}(\%).$$

The following 4 experimental groups were investigated:

Group 1—Iontophoresis on intact skin: The iontophoresis patch was immersed with 1.5 ml (150 IU) of Humalog (Insulin—Lispro, 100 IU/ml). Three consecutive patches were used, each was applied for 90 minutes. The total dose of insulin Lispro administered was 450 IU.

Group 2—ViaDerm treated skin (passive diffusion): ViaDerm was applied on eight adjacent sites which were then covered with the iontophoresis patch containing 150 IU insulin Lispro. Three consecutive patches were used, each was applied for 90 minutes. The total dose of insulin Lispro administered was 450 IU. The power supply was not turned on.

Group 3—ViaDerm treated skin and iontophoresis: ViaDerm was applied on eight adjacent sites which were then covered with the iontophoresis patch containing 150 IU insulin Lispro. Three consecutive patches were used, each was applied for 90 minutes. The total Lispro administered dose was 450 IU. Power supply was turned on.

Group 4—Subcutaneous injections of 10 IU of insulin. Three pigs were tested in groups I, III and IV, and one pig was tested in group II.

Results

The results of transdermal delivery of insulin to pigs are shown in FIG. 1 and summarized in Table 1. A synergetic effect was observed when the ViaDerm and iontophoresis technologies were applied. High levels of insulin in the plasma of pigs treated with ViaDerm and iontophoresis were measured (FIG. 1) and the dose efficiency was 18% as compared to SC injection (Table 1). Application of iontophoresis on intact skin resulted in a negligible increase in insulin levels in the blood (FIG. 1). Passive diffusion of insulin from iontophoresis patches through ViaDerm treated skin resulted in about 20 fold lower delivery of insulin compared to that obtained with ViaDerm and iontophoresis.

TABLE 1

AUC and dose efficiency following transdermal delivery of insulin.

| Group | # of Pigs | AUC (uIU*hr/ml) | Dose Efficiency (%) | IU Delivered (relative to SC) |
|---|---|---|---|---|
| SC | 3 | 228 ± 20 | 100 | 10 |
| ViaDerm treated skin + Iontophoresis | 3 | 1823 ± 672 | 18 ± 7 | 80 ± 30 |
| Iontophoresis on intact skin | 3 | 0 ± 0 | 0 ± 0 | 0 ± 0 |
| ViaDerm treated skin (passive diffusion) | 1 | 113 | 1 | 5 |

Example 2

Transdermal Delivery of hGH by ViaDerm and Iontophoresis in Anesthetized Rats

The present experiment aimed at studying whether iontophoresis using Iogel® (Iomed LTD) patches is capable of increasing the transdermal permeation of hGH compared to a passive delivery from the same electrodes on ViaDerm treated skin. Two groups of rats were tested. Iogel patches, each loaded with 1.5 mg of hGH (Genotropin®, Pharmacia and Upjohn) in 1.5 ml water for injection (Demo S.A., Greece) were applied to both groups. One group was connected to a power supply (constructed in house) and the other was not. The hGH loaded patch was connected to the negative pole of the power supply.

Experimental Procedure

Rats (males, 300-325 gr, Sprague Dawley) were kept under anesthesia throughout the experiment. The following experimental groups were investigated:

Group 1—Passive delivery: 3 rats were treated with ViaDerm on two adjacent sites (total area 2.8 cm$^2$) over which the iontophoresis patch was placed. The reference electrode assembly was placed on a shaved intact skin on the back of the anal. The power supply was not turned on.

Group 2—Iontophoresis delivery: 3 rats were treated with ViaDerm on two adjacent sites (total area 2.8 cm$^2$) over which the iontophoresis patch was placed. The reference electrode assembly was placed on a shaved intact skin on the back of the animal. The power supply was turned on.

ViaDenm operating parameters: Burst length—700 μsec; Voltage—330V; Number of bursts—2; Two applications on the same skin area (150 pores/cm$^2$); Without current limitation; 80 μm diameter electrode arrays; Current density used: 0.18 mA/cm$^2$.

To detect hGH levels in serum—Elisa kit (DSL Inc. Webster, Tex., USA) was used.

Results

All pretreatment trans epidermal water loss (TEWL) values were below 8.5 g/h/m$^2$ and the A TEWL was >20 g/hm$^2$ for two ViaDenn applications. The power supply used in this experiment was set to instantly deliver 0.5 mA to each animal (0.18 mA/cm$^2$). Two hours and five minutes were required to reach the current. At the end of the experiment, after removal of the iontophoretic patches, burn marks were seen at the contact area of the electrode probably due to insufficient contact.

TABLE 2

Serum hGH levels (ng/ml)

| Time (hours) | Patch + Iontophoresis Avg. | Passive Patch Avg. |
|---|---|---|
| 0 | 0.1 | 0.1 |
| 0.75 | 22.7 | 5.1 |
| 1.5 | 61.1 | 14.0 |
| 2.25 | 109.8 | 23.3 |
| 3 | 128.9 | 40.8 |
| 4.5 | 143.9 | 52.8 |
| 6 | 175.1 | 34.0 |

The results show that ViaDerm and iontophoresis improved hGH permeation compared to ViaDerm only (the passive delivery). The AUC values were 637 ng×hr/ml for the group treated with ViaDerm and iontophoresis versus 182 ng×hr/ml for the group of ViaDerm only (passive delivery; 3.5 fold higher).

As shown in Table 2, the profile of hGH in serum in the ViaDerm group (passive delivery) started to decrease after 4.5 hours while the profile of hGH in the ViaDerm and iontophoresis group continued to increase for the entire duration of the experiment. It is to be understood that the rats in the present experiment were anesthetized. Though we do not wish to be bound to any mechanism of action, anesthetics may influence the drug delivery profile because of a slower metabolism rate and alteration of body temperature homeostasis. It is known that anesthetized animals lose more heat to the surrounding environment resulting in vasoconstriction of peripheral blood vessels, which may impair hGH delivery.

Figure 2:
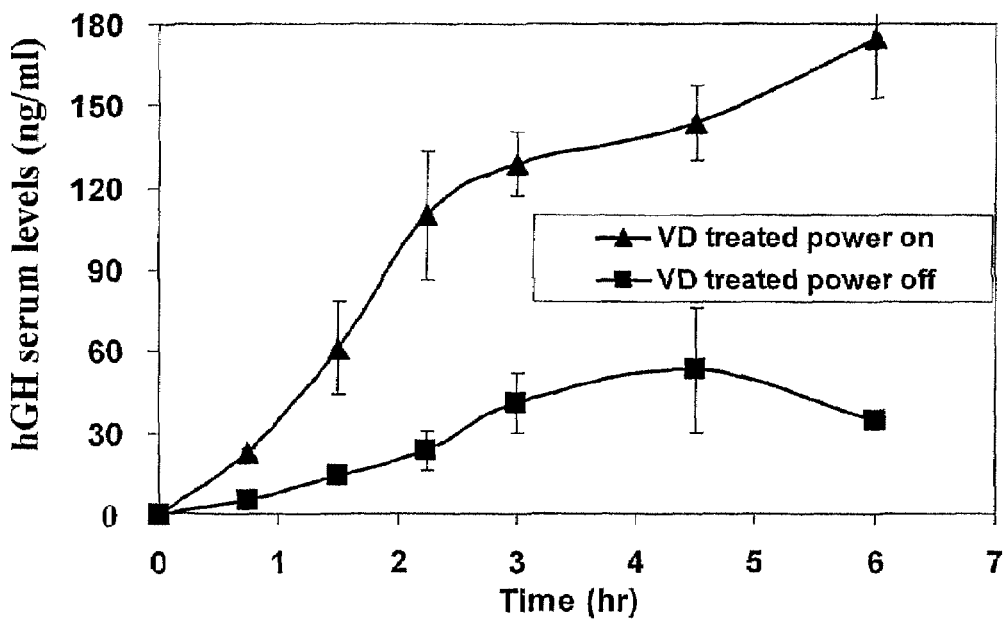
FIG. 2 shows transdermal delivery of human growth hormone (hGH) in rats. hGH was delivered through skin of rats either by ViaDerm treatment followed by application of an iontophoretic patch containing hGH when current was not supplied (squares), or by ViaDerm treatment followed by application of an iontophoretic patch containing hGH when current was supplied (triangles). hGH serum concentrations were measured.

As shown in FIG. 2, hGH delivery continued for more than 6 hours. This indicates that during this period of time, the micro-channels generated by ViaDerm were still open to enable hGH delivery.

The results of this experiment clearly show that the combination of iontophoresis and ViaDerm significantly increases the permeation of hGH from the iontophoresis patch as compared to hGH delivery in ViaDerm treated skin (passive delivery).

Example 3

Transdermal Delivery of hGH by ViaDerm and Iontophoresis in Rats

This study was aimed at studying whether a more concentrated solution of hGH can improve hGH delivery and bioavailability. Three groups: 1) ViaDerm treatment-passive delivery; 2) iontophoresis on intact skin; and 3) ViaDerm and iontophoresis; received 15 mg hGH (1.5 ml) in an Iogel patch, one group received 1.5 mg in an Iogel patch (iontophoresis), and another group—SC group, received 150 μg of hGH. In the present experiment a power supply (parallel connection instead of serial) was used in order to improve the power supply.

Experimental Procedure

Rats (males, 250-300 gr, Sprague Dawley; 3 rats per experimental group) were used in the present experiment:

Group 1—Passive delivery: Two adjacent sites on the rat's skin were treated with ViaDerm and then covered with an iontophoresis patch containing 15 mg hGH (1.5 ml). The power supply was not turned on.

Group 2—Iontophoresis without ViaDerm treatment: 15 mg hGH were loaded into the Iogel patch and applied on intact skin. Power supply was turned on.

Group 3—ViaDerm and iontophoresis—high dose delivery:
Two adjacent sites on the rat's skin were treated with ViaDerm and then covered with an iontophoresis patch containing 15 mg hGH. The power supply was turned on.
Group 4—ViaDerm and iontophoresis—low dose delivery:
Two adjacent sites on the rat's skin were treated with ViaDerm and then covered with an iontophoresis patch containing 1.5 mg hGH. The power supply was turned on.
Group 5—SC injection of 150 μg hGH.

Human GH solution was prepared from a 12 mg Genotropin vial (Genotropin®, Pharmacia and Upjohn). The levels of hGH in serum were analyzed using Elisa kit (DSL Inc. Webster Tex., USA). HPLC was used to quantitate SC solution.

ViaDerm operating parameters: Burst length—700 μsec; Voltage—330V; Number of bursts—2; 2 applications on the same skin area (150 micro-channels/cm$^2$); Two application sites (total area 2.8 cm$^2$); Without current limitation; 80 μm diameter electrode of the electrode arrays.

Iontophoresis application parameters: Current density 0.64 mA/cm$^2$ (total 1.8 mA). Current elevation time (from 0-max) 20 seconds. Current application time 8 hours.

Clinical Observations

Black burning marks (3$^{rd}$ degree burns) were observed on the rat's abdomen at the site of the patch application. In ViaDerm treated animals the burns appeared at some or at all of the ViaDerm application sites irrespective of hGH concentration. In intact skin animals the burns were confined to the area under the round metal connector of the Iogel patch. Sporadic burn marks also appeared on the reference electrode site irrespective of the group. No burn marks appeared on animals in which the power supply was off.

Results

All pretreatment TEWL values were below 8.5 g/h/m$^2$ and the Δ TEWL was >20 g/hm$^2$ for two ViaDerm applications.

TABLE 3 hGH plasma levels

| Time (hr) | 15 mg hGH, Iontoph. off, +VD | | 15 mg hGH, Iontoph. on, intact | | 15 mg hGH, Iontoph. on, +VD | | 1.5 mg hGH, Iontoph. on, +VD | | S.C. 150 ug/0.2 ml hGH | |
|---|---|---|---|---|---|---|---|---|---|---|
| | Avg. | S.D. | Avg. | S.D. | Avg. | S.D. | Avg. | S.D. | Avg. | S.D. |
| 0.0 | 0.1 | 0.0 | 0.1 | 0.0 | 0.0 | 0.0 | 0.1 | 0.1 | 0.1 | 0.0 |
| 1.0 | 89.7 | 38.3 | 1.9 | 1.7 | 504.8 | 227.7 | 225.1 | 54.4 | 153.0 | 33.2 |
| 2.0 | 178.7 | 31.3 | 7.2 | 8.8 | 958.5 | 125.6 | 346.3 | 44.7 | 156.8 | 22.2 |
| 3.0 | 283.7 | 87.3 | 8.3 | 10.5 | 2011.6 | 771.7 | 617.3 | 115.2 | 127.8 | 7.7 |
| 4.0 | 389.4 | 168.9 | 9.2 | 12.9 | 2204.9 | 986.7 | 444.5 | 96.4 | 120.1 | 43.8 |
| 6.0 | 573.1 | 297.5 | 5.4 | 7.1 | 1802.0 | 902.3 | 184.3 | 93.3 | 75.3 | 72.2 |
| 8.0 | 873.4 | 708.3 | 4.7 | 3.1 | 1244.1 | 712.6 | 111.3 | 52.9 | 43.4 | 33.7 |

TABLE 4

AUC (ng-hr/ml) and bioavailability

| group | AUC (ng-hr/ml) | Bioavailability (%) |
|---|---|---|
| Intact + Iontophoresis 15 mg | 47 | 0.05 |
| ViaDerm + Iontophoresis off 15 mg | 3156 | 3.9 |
| ViaDerm + Iontophoresis on 15 mg | 11630 | 14.3 |
| ViaDerm + Iontophoresis on 1.5 mg | 2336 | 28.8 |
| SC 150 ug | 812 | 100 |

Figure 3:
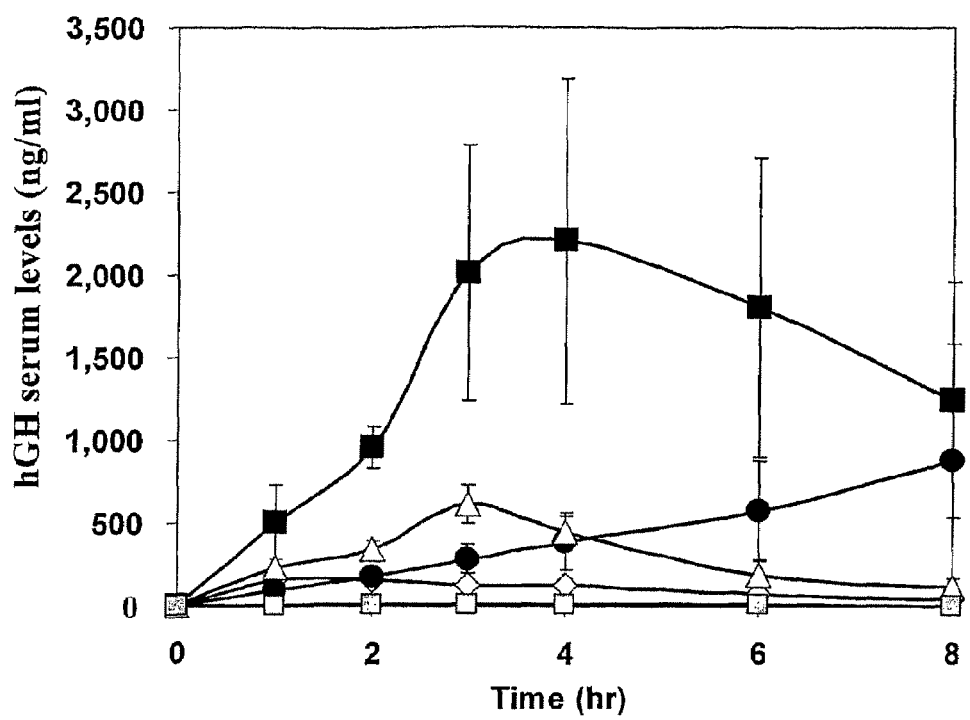
FIG. 3 shows transdermal delivery of hGH in rats as a function of hGH concentration in the iontophoretic patch. hGH was delivered through skin of rats either by ViaDerm treatment followed by application of an iontophoretic patch containing hGH when current was not supplied (circles), by application on intact skin of an iontophoretic patch containing hGH when current was supplied (gray squares), by ViaDerm treatment followed by application of an iontophoretic patch containing low or high dose of hGH when current was supplied (triangles and filled squares, respectively), or by subcutaneous injection (diamonds). The levels of hGH in serum were measured.

The results presented in FIG. 3 and in Tables 3 and 4 clearly demonstrate that iontophoresis alone does not cause hGH delivery. Comparison of hGH delivery between the ViaDerm treated group, in which the power supply was not turned on (Iontophoresis off+ViaDerm; passive delivery), and the ViaDerm treated group, in which iontophoresis was applied (Iontophoresis on+ViaDerm), showed that the amount of the hormone delivered was significantly higher when iontophoresis was turned on. The delivery profile from the Iogel patch showed a constant increase over time (Iontophoresis off+ViaDerm) suggesting stability of the hGH in the Iogel patch.

Comparison between the two concentration groups clearly demonstrates the advantage in using high concentration of hGH. This advantage was evident in the amount of hGH delivered, but not in bioavailability, which was higher in the 1.5 mg hGH group.

The burning marks on the skin were probably due to the extended periods of time of current application. At the current density as set in the present experiment the electrodes were supposed to function for about 1 hour until their AgCl is exhausted. After that point the electrolysis continued by water hydrolization, a process that probably caused the observed skin burns.

Example 4

Transdermal Delivery of hGH by ViaDerm and Iontophoresis in Anesthetized Pigs

This study aimed at studying the transdermal hGH delivery in pigs using the ViaDerm and Iontophoresis technologies.

ViaDerm applications were performed on 8 adjacent sites on the marginal ear of each of the pigs using 80 μm electrodes and 2 bursts. The hGH iontophoresis patches were replaced sequentially for 5 times.

Experimental Procedure 2 groups of pigs (males, 10-15 kg, large white) were tested:
Group 1: SC (250 μg)—3 pigs (no. 3, 9 and 25).
Group 2: ViaDerm and then iontophoresis was applied 5 times, each iontophoresis patch contained 22.5 mg (22.5× 5; total of 112.5 mg)—3 pigs (no. 19, 20 and 21).

Results

TABLE 5 hGH plasma levels results (ng/ml)
Subcutaneous injection 0.25 mg hGH

| Time (hours) | Animal number | | | | |
|---|---|---|---|---|---|
| | pig3 SC 0.25 mg hGH | pig9 SC 0.25 mg hGH | pig25 SC 0.25 mg hGH | Average | SD |
| 0 | 0.14 | 0.08 | 0.10 | 0.1 | 0.0 |
| 1 | 6.40 | 22.96 | 38.06 | 22.5 | 15.8 |
| 2 | 10.57 | 18.06 | 31.00 | 19.9 | 10.3 |
| 3 | 6.02 | 15.88 | 16.32 | 12.7 | 5.8 |
| 4 | 5.39 | 12.39 | 13.40 | 10.4 | 4.4 |
| 5 | 2.57 | 9.85 | 8.69 | 7.0 | 3.9 |
| 6 | 3.35 | 6.53 | 6.66 | 5.5 | 1.9 |
| 7 | 2.40 | 6.31 | 3.89 | 4.2 | 2.0 |
| 8 | 2.00 | 4.19 | 2.76 | 3.0 | 1.1 |
| 9 | 1.48 | 2.58 | 1.67 | 1.9 | 0.6 |
| 10 | 1.18 | 1.83 | 1.19 | 1.4 | 0.4 |
| 11 | 1.49 | 1.25 | 1.09 | 1.3 | 0.2 |
| 12 | 1.75 | 0.88 | 0.78 | 1.1 | 0.5 |

| Time (hours) | Animal number | | | | |
|---|---|---|---|---|---|
| | pig19 Iontoph. × 5 Total 112.5 mg hGH | pig20 Iontoph. × 5 Total 112.5 mg hGH | pig21 Iontoph. × 5 Total 112.5 mg hGH | Average | SD |
| 0 | 0.04 | 0.06 | 0.08 | 0.06 | 0.02 |
| 1 | 8.39 | 7.01 | 2.68 | 6.03 | 2.98 |
| 2 | 18.46 | 22.45 | 10.38 | 17.10 | 6.15 |
| 3 | 24.50 | 26.93 | 24.52 | 25.32 | 1.40 |
| 4 | 25.34 | 31.04 | 28.87 | 28.41 | 2.88 |
| 5 | 25.27 | 28.21 | 44.93 | 32.80 | 10.60 |
| 6 | 13.34 | 22.09 | 34.25 | 23.23 | 10.50 |
| 7 | 9.63 | 44.00 | 33.54 | 29.06 | 17.62 |
| 8 | 4.03 | 10.69 | 28.93 | 14.55 | 12.89 |
| 9 | 4.08 | 8.98 | 24.89 | 12.65 | 10.88 |
| 10 | 3.32 | 6.49 | 22.46 | 10.75 | 10.26 |
| 11 | 1.42 | 4.91 | 17.86 | 8.06 | 8.66 |
| 12 | 1.38 | 5.01 | 9.00 | 5.13 | 3.81 |

TABLE 6

AUC and bioavailability.

| Treatment | pig no. | AUC (ng-hr/ml) | average AUC | Amount delivered (μg) |
|---|---|---|---|---|
| SC 250 μg | 3 | 44 | 90.3 | 250 |
| | 9 | 102 | | |
| | 25 | 125 | | |
| Ionto 22.5 mg × 5 | 19 | 138 | 210.3 | 589 |
| | 20 | 215 | | |
| | 21 | 278 | | |

Figure 4:
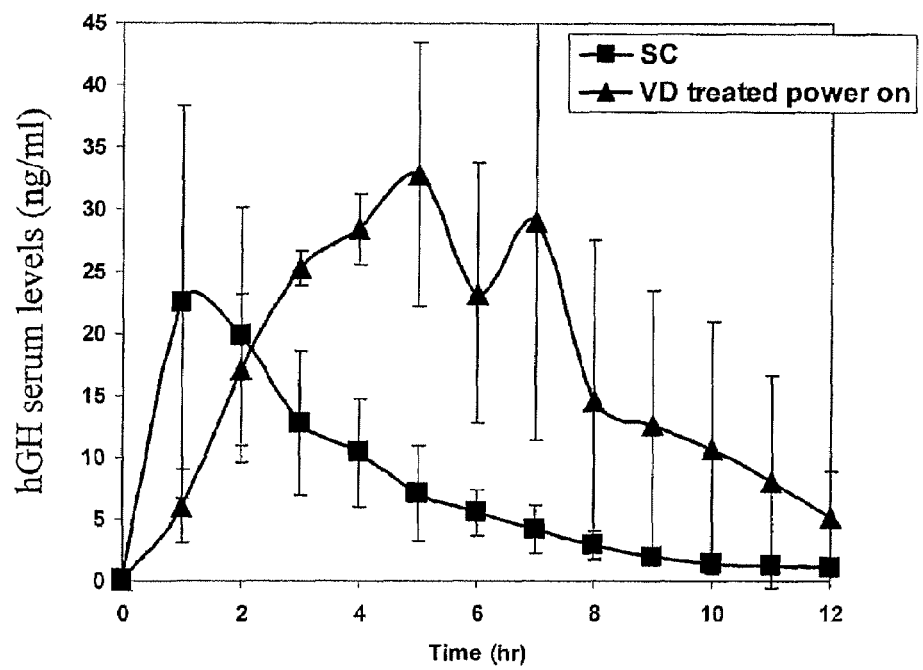
FIG. 4 shows transdermal delivery of hGH in pigs. hGH was delivered through skin of pigs either by ViaDerm treatment followed by application of an iontophoretic patch containing hGH when current was supplied (triangles), or by subcutaneous injection (squares). The levels of hGH in plasma were measured.

As shown in FIG. 4 and Table 6, the SC group had an average AUC value of 90.3 ng×hr/ml.

The ViaDerm and Iontophoresis group was subjected to 5 consecutive patches (AUC 210.3 ng*hr/ml, $T_{max}$ was 5-7 hours and the $C_{max}$ was 32.8 ng/ml). The amount of hGH that was delivered by the combination of ViaDerm and Iontophoresis technologies was significantly higher than the amount delivered by SC injection, thus demonstrating the advantage of the system.

It is to be understood that the commercial patches used in this study required a large loading volume (1.5 ml), and therefore high hGH concentrations were used (22.5 mg hGH per electrode). In addition, the commercial patches included a gel that increased the contact with the skin. However, the gel probably impaired protein delivery.

Also, the application of the last two iontophoresis patches did not significantly improve hGH delivery, and therefore the present results suggest that similar hGH delivery would have been obtained by applying only 3 iontophoresis patches, resulting in higher overall efficiency.

It should be also noted that no irritation was observed in the treated group neither at the drug nor the reference electrode. The pH values at the iontophoretic patch were stable and range between 6-6.5 throughout the experiment.

The reference electrode required constant wetting with saline to keep the voltage values constant throughout the experiment, probably due to the drier skin and lack of sweating in pigs compared to human. As the reference electrode is approved for use in humans it is assumed that a wetting problem does not encounter in humans.

Example 5

Transdermal Delivery of Insulin by ViaDerm and Iontophoresis in Human Subjects

This study was aimed at studying the pharmacokinetic and pharmacodynamic profile of insulin delivered transdermally from an iontophoretic drug delivery device in combination with treatment of the skin with ViaDerm™ device and comparing the insulin pharmacokinetic and pharmacodynamic profile to that obtained by iontophoretic system only or by ViaDerm treatment only in human subjects using euglycemic clamping technique.

Insulin (150 IU of Humalog Lispro-100) was loaded into an iontophoretic patch (7.5 cm$^2$ per patch).

ViaDerm operating parameters: 290V for 9 msc. The Array was of 1.4 cm$^2$ square matrix arrangement. Each of the electrodes in the electrode array was cylindrical having a diameter of 80 microns and a length of 95 microns. The density of the electrodes was 75 electrodes/cm$^2$. The device was applied twice on each location and therefore the density of the micro channels generated was 150 per cm$^2$.

Blood samples were drawn at different time points and analyzed for blood glucose (Accutrend Sensor, Roche Diagnostics) and insulin levels (Insulin kit: Insulin radioimmunoassay, INSIK-5, DiaSorin; C-Peptide: double antibody, DPC). The blood glucose level was determined onsite immediately after blood was drawn. Based on the blood glucose levels measured, infusion rate of glucose was constantly reset to maintain blood glucose at a target glucose clamp level of 90±10 mg/dl (euglycemic clamping technique).

Dermal safety for transdermal delivery treatments was evaluated by measuring the erythema and edema at the treatment site immediately after treatment, immediately after patch removal and 24 hours after patch removal calculating the Primary Irritation Index scores (Draize scoring).

The study was performed as a four way cross over study in which a group of five healthy male human subjects were treated with three different transdermal treatments and subcutaneous (SC) treatment with a minimum of 5 days washout period between treatments as follows:

Group 1—ViaDerm and iontophoresis: human subjects were treated with the ViaDerm™ device and then an iontophoresis patch containing 150 IU of the insulin analog (Humalog Lispro-100) was applied on a skin area of 7.5 cm². Current of 1.4 mA was applied for 270 min. After 270 min the patch remained in place for 450 more minutes.

Group 2—Iontophoresis: iontophoresis patch containing 150 IU of the insulin analog (Humalog Lispro-100) was applied on a skin area of 7.5 cm². Current of 1.4 mA was applied for 270 min. After 270 min the patch remained in place for 450 more minutes.

Group 3—ViaDerm (passive delivery): human subjects were treated with the ViaDerm™ device and then an iontophoresis patch containing 150 IU of the insulin analog (Humalog Lispro-100) was applied on a skin area of 7.5 cm². The patch remained in place for 720 minutes. The power supply was not turned on.

Group 4—SC injection: 10 U of the insulin analog were injected SC.

Results

Figure 5:
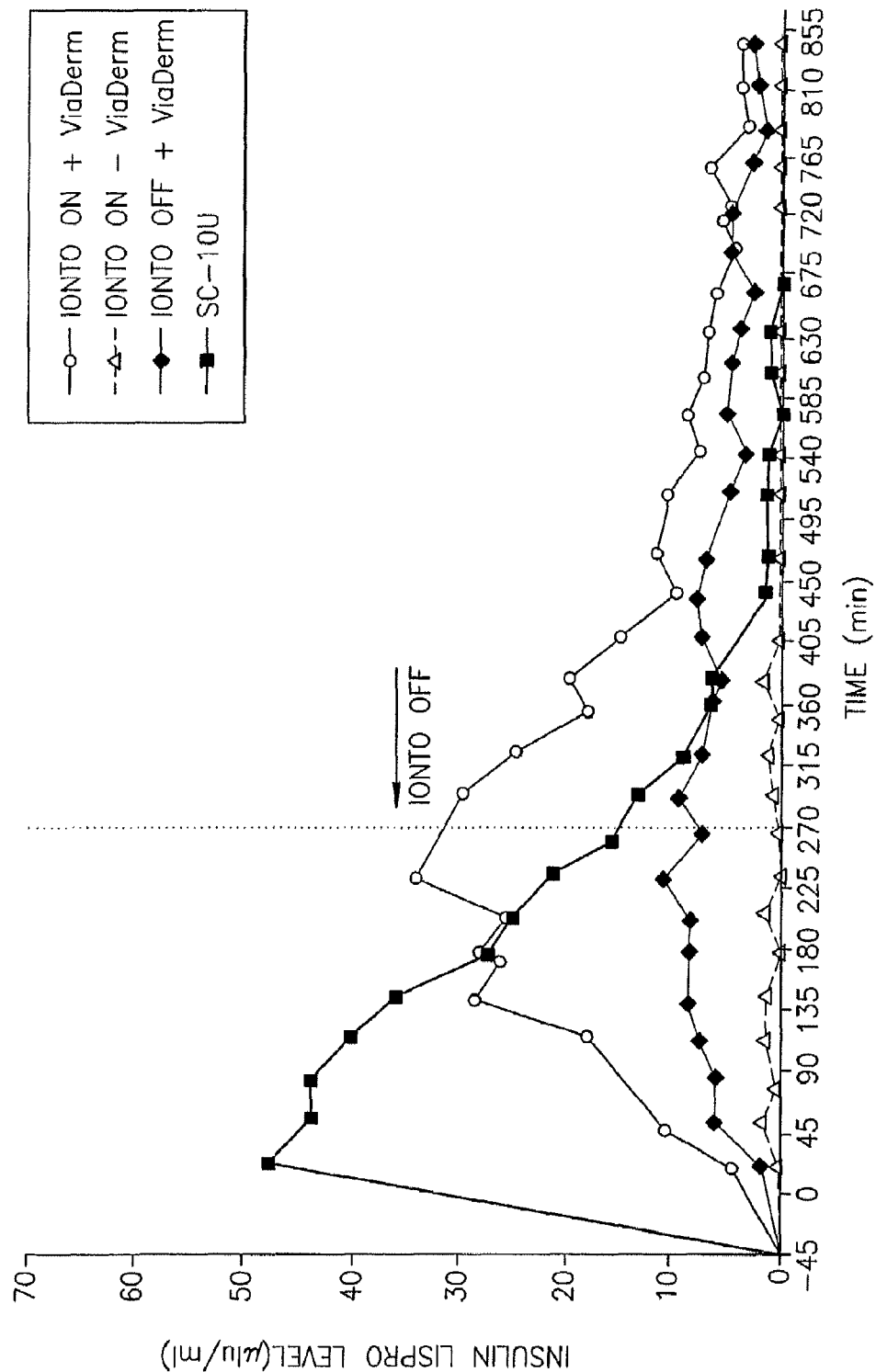
FIG. 5 shows transdermal delivery of insulin to human subjects. Insulin (Lispro) was delivered through the skin of human subjects either by ViaDerm treatment followed by application of an iontophoretic patch containing insulin when no current was supplied (diamonds), by application on intact skin of an iontophoretic patch containing insulin when current was supplied (triangles), by ViaDerm treatment followed by application of an iontophoretic patch containing insulin when current was supplied (circles), or by subcutaneous injection (SC). Insulin plasma concentrations were measured.

Plasma insulin concentration profile resembled a classical drug delivery profile from an iontophoresis patch applied with current. Insulin delivery in the group of ViaDerm and iontophoresis increased with the application of current and decreased when the current was turned off. The mean total insulin (Humalog Lispro-100) level delivered was found to be 11322 μIU×min/ml (AUC; after subtracting baseline insulin). The mean peak plasma concentration (Cmax) of 36.9 μIU/ml was reached at 211 minutes (Tmax). The amount of insulin delivered was found to be 11 units (Table 7 and FIG. 5).

Plasma insulin concentration profile in human subjects treated with iontophoresis only was low and the level of insulin (Humalog Lispro-100) delivered was found to be negligible (after subtracting baseline insulin). The mean total insulin level delivered in this group was found to be 213 μIU×min/ml (AUC). The mean peak plasma concentration (Cmax) of 2.5 μIU/ml was reached at 85 minutes (Tmax). The amount of insulin delivered was found to be 0.2 units (Table 7 and FIG. 5).

ViaDerm treatment and then application of the iontophoresis patch without providing current (passive delivery) showed that the plasma insulin concentration profile resembled a classical drug delivery profile from a passive transdermal patch. The mean insulin delivered transdermally from the patch was found to be 4436 μIU×min/ml (AUC; after subtracting baseline insulin). The mean peak plasma concentration (Cmax) of 12 μIU/mL was reached at 21 minutes (Tmax). The amount of insulin delivered was calculated and was found to be 4.3 units (Table 7 and FIG. 5).

TABLE 7

Pharmacokinetic and pharmacodynamic values in human subjects.

|  |  | ionto on + ViaDerm | | ionto on − ViaDerm | | ionto off + ViaDerm | | SC-10U | |
| --- | --- | --- | --- | --- | --- | --- | --- | --- | --- |
|  |  | mean | SD | mean | SD | mean | SD | mean | SD |
| Pharmacokinetic data | | | | | | | | | |
| $C_{max}$ | μU/ml | 36.9 | 5.0 | 2.5 | 1.2 | 12.0 | 2.3 | 65.3 | 46.1 |
| $t_{max}$ | min | 211 | 39 | 85 | 56 | 211 | 65 | 73 | 45 |
| AUC | μU/ml/720 min | 11322 | 2339 | 213 | 786 | 4436 | 841 | 10181 | 2903 |
| Total units delivered | | 11 | | 0.2 | | 4.3 | | 10 | |
| Pharmacodynamic data | | | | | | | | | |
| $GIR_{max}$ | mg/kg/min | 4.7 | 1.7 | 1.1 | 0.7 | 2.5 | 0.6 | 3.7 | 0.8 |
| $t_{max}$ | min | 281 | 24 | 507 | 314 | 358 | 44 | 195 | 10 |
| AUC | mg/kg/720 min | 2098 | 675 | 344 | 240 | 1303 | 325 | 1488 | 513 |

The plasma insulin concentration profile in the SC group resembled a classical drug delivery profile in subcutaneous administration. The mean insulin bioavailability was found to be 10181 μIU×mm/ml (AUC; after subtracting of baseline insulin). The mean peak plasma concentration (Cmax) of 65.3 μIU/mL was reached at an average time (Tmax) of 73 minutes.

Figure 6:
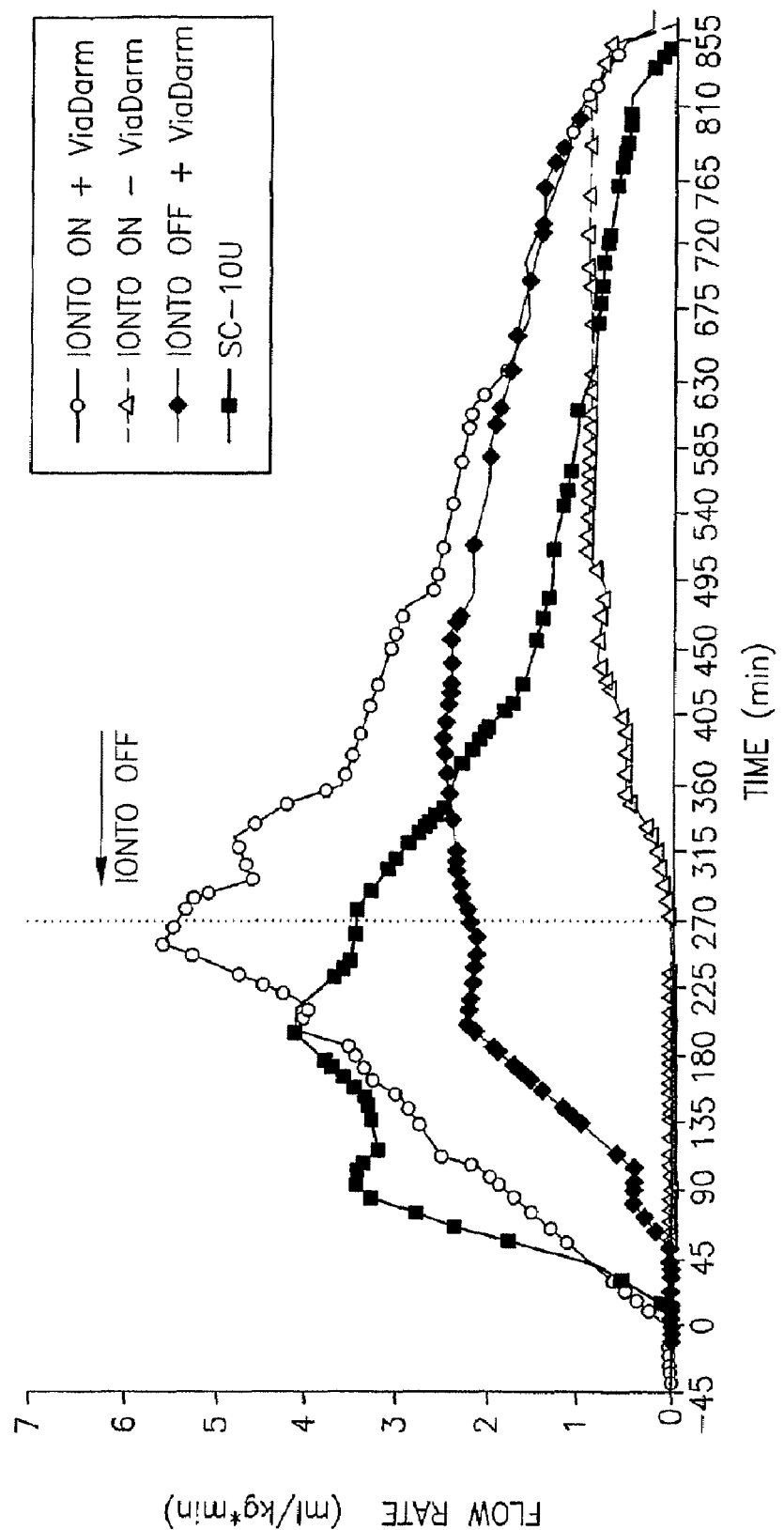
FIG. 6 shows glucose infusion rate during insulin delivery to human subjects. Glucose was infused to human subjects to which insulin (Lispro) was delivered transdermally either by ViaDerm treatment followed by application of an iontophoretic patch containing insulin when no current was supplied (diamonds), by application on intact skin of an iontophoretic patch containing insulin when current was supplied (triangles), by ViaDerm treatment followed by application of an iontophoretic patch containing insulin when current was supplied (circles), or by subcutaneous injection (SC). The rate of glucose infusion was measured.

The biopotency of these treatments was assessed by determining glucose infusion rate (FIG. 6).

Dermal Safety

Analysis of the erythema and edema Draize scores observed for insulin delivery in the group treated with the iontophoresis patch with current and with ViaDerm treatment indicated a "slight" (0.5-1.9 out of a scale of 8) potential for irritation effects 24 hours post patch removal Analysis of the Erythema and Edema Draize scores observed for insulin delivery in the group treated with the iontophoresis patch with current and without ViaDerm treatment indicated a "negligible"(0-0.4 out of a scale of 8) potential for irritation effects 24 hours post patch removal.

Analysis of the Erythema and Edema Draize scores observed for insulin delivery in the group treated with the iontophoretic patch with no current and with ViaDerm treatment indicated a "slight"(0.5-1.9 out of a scale of 8) potential for irritation effects 24 hours post patch removal.

Conclusions

Application of the iontophoretic technology in combination with ViaDerm pretreatment using an iontophoresis patch enhanced insulin delivery by a factor of 2.5 in comparison to ViaDerm alone No delivery was observed using the iontophoretic technology alone.

Only slight Erythema and Edema were detected using the ViaDerm system, with and without application of the iontophoretic current.

Example 6

Transdermal Delivery of Insulin by ViaDerm and Iontophoresis in Human Subjects This study was aimed at studying the pharmacokinetic and pharmacodynamic profile of insulin delivered transdermally from an iontophoretic drug delivery device in combination with treatment of the skin with ViaDerm™ device and comparing the insulin pharmacokinetic and pharmacodynamic profile to that obtained by ViaDerm treatment in human subjects using euglycemic clamping technique.

Insulin (750 IU of Humulin-500) was loaded into an iontophoresis gel patch (TransQI, Iomed USA; 7.5 cm² per patch).

ViaDerm operating parameters: 290V for 9 msc. The Array was of 1.4 cm² square matrix arrangement. Each of the electrodes in the electrode array was cylindrical having a diameter of 80 microns and a length of 95 microns. The density of the electrodes was 75 electrodes/cm². The device was applied twice on each location and therefore the density of the micro channels generated was 150 per cm².

Blood samples were drawn at different time points and analyzed for blood glucose and insulin levels. The blood glucose level was determined onsite immediately after blood was drawn. Based on the blood glucose levels measured, infusion rate of glucose was constantly reset to maintain blood glucose at a target glucose clamp level of 90±10 mg/dl (euglycemic clamping technique).

Dermal safety for transdermal delivery treatments was evaluated by measuring the erythema and edema at the treatment site immediately after treatment, immediately after patch removal and 24 hours after patch removal calculating the Primary Irritation Index scores (Draize scoring).

The study was performed as a three way cross over study in which a group of five healthy male human subjects were treated with two different transdermal treatments and subcutaneous (SC) treatment with a minimum of 5 days washout period between treatments as follows:

Group 1—ViaDerm and iontophoresis: human subjects were treated with the ViaDerm™ device and then an iontophoresis patch containing 750 IU of the insulin (Humulin R 500 IU) was applied on a skin area of 7.5 cm². Current of 1.4 mA was applied for 270 min. After 270 min the patch remained in place for 450 more minutes.

Group 2—ViaDerm (passive delivery): human subjects were treated with the ViaDerm™ device and then an iontophoresis patch containing 750 IU of insulin (Humulin R 500 IU) was applied on a skin area of 7.5 cm². The patch remained in place for 720 minutes. The power supply was not turned on.

Group 3—SC injection: 10 U of Humulin R (U-100) were injected SC.

Results

Figure 7:
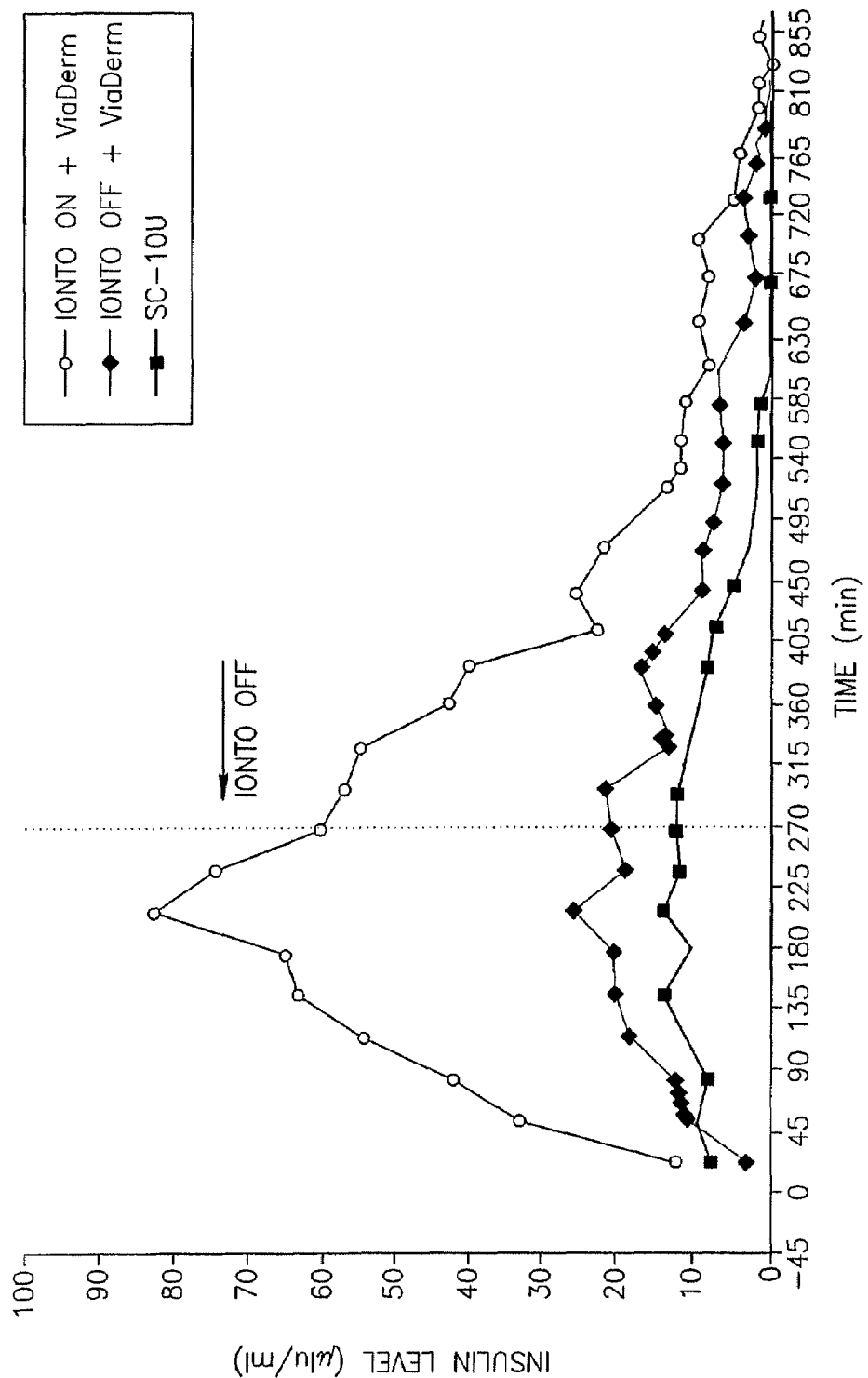
FIG. 7 shows transdermal delivery of insulin to human subjects. Insulin (Humulin R) was delivered through the skin of human subjects either by ViaDerm treatment followed by application of an iontophoretic patch containing insulin when no current was supplied (diamonds), by ViaDerm treatment followed by application of an iontophoretic patch containing insulin when current was supplied (circles), or by subcutaneous injection (SC). Insulin plasma concentrations were measured.

Insulin concentration profile in the group treated with iontophoresis and ViaDerm resembled a classical drug delivery profile from an iontophoresis patch applied with current. The correlation between the onset of drug delivery and application of current and the correlation between the decrease in drug delivery and turning off the current clearly indicates a rapid on/off control for insulin delivery with the control of iontophoresis current. The mean total exogenous insulin level delivered in this group was found to be 24567 μIU×min/ml (AUC; after subtracting baseline insulin). The mean peak plasma concentration (Cmax) of 83.0 μIU/ml was reached at 199 minutes (Tmax). The amount of insulin delivered was found to be 48 units (Table 8 and FIG. 7).

Plasma insulin concentration profile in the group treated with ViaDerm and the iontophoresis patch without current (passive delivery) resembled a classical drug delivery profile from a passive transdermal patch. The mean total exogenous insulin delivered transdermally in this group was found to be 8493 μIU×min/ml (AUC; after subtracting of baseline insulin). The mean peak plasma concentration (Cmax) of 27.0 μIU/ml was reached at 217 minutes (Tmax). The amount of insulin delivered was calculated and was found to be 17 units (Table 8 and FIG. 7).

The plasma insulin concentration profile in the group injected SC with 10U of Humulin R (U-100) resembled a classical drug delivery profile after subcutaneous administration. The mean total exogenous insulin bioavailability in this group was found to be 511 μIU×min/ml (AUC; after subtracting of baseline insulin). The mean peak plasma concentration (Cmax) of 17.8 μIU/ml was reached at an average time (Tmax) of 214 minutes (Table 8 and FIG. 7).

Figure 8:
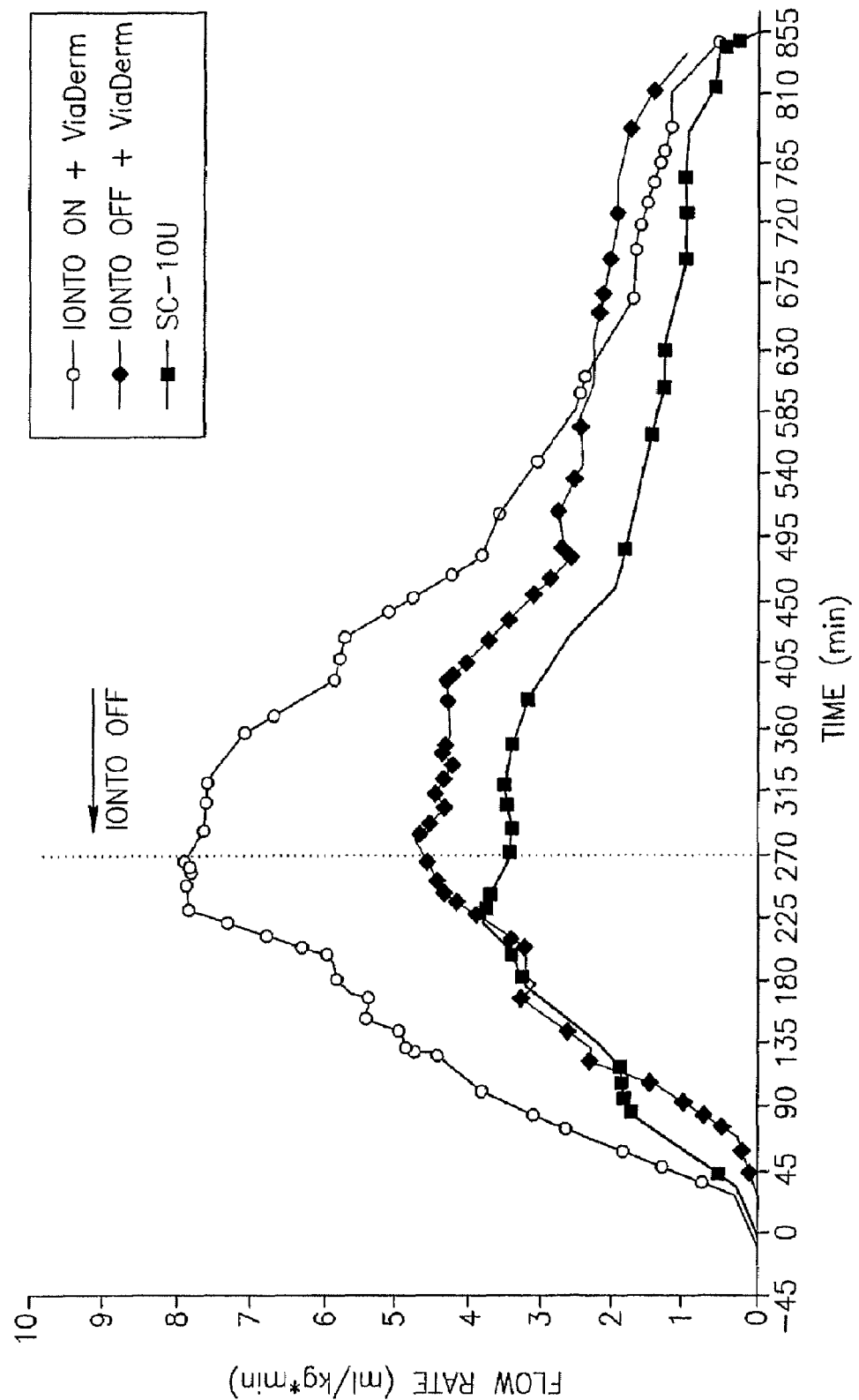
FIG. 8 shows glucose infusion rate during insulin delivery to human subjects. Glucose was infused to human subjects to which insulin (Humulin R) was delivered transdermally either by ViaDerm treatment followed by application of an iontophoretic patch containing insulin when no current was supplied (diamonds), by ViaDerm treatment followed by application of an iontophoretic patch containing insulin when current was supplied (circles), or by subcutaneous injection (SC). The rate of glucose infusion was measured.
Figure 9:
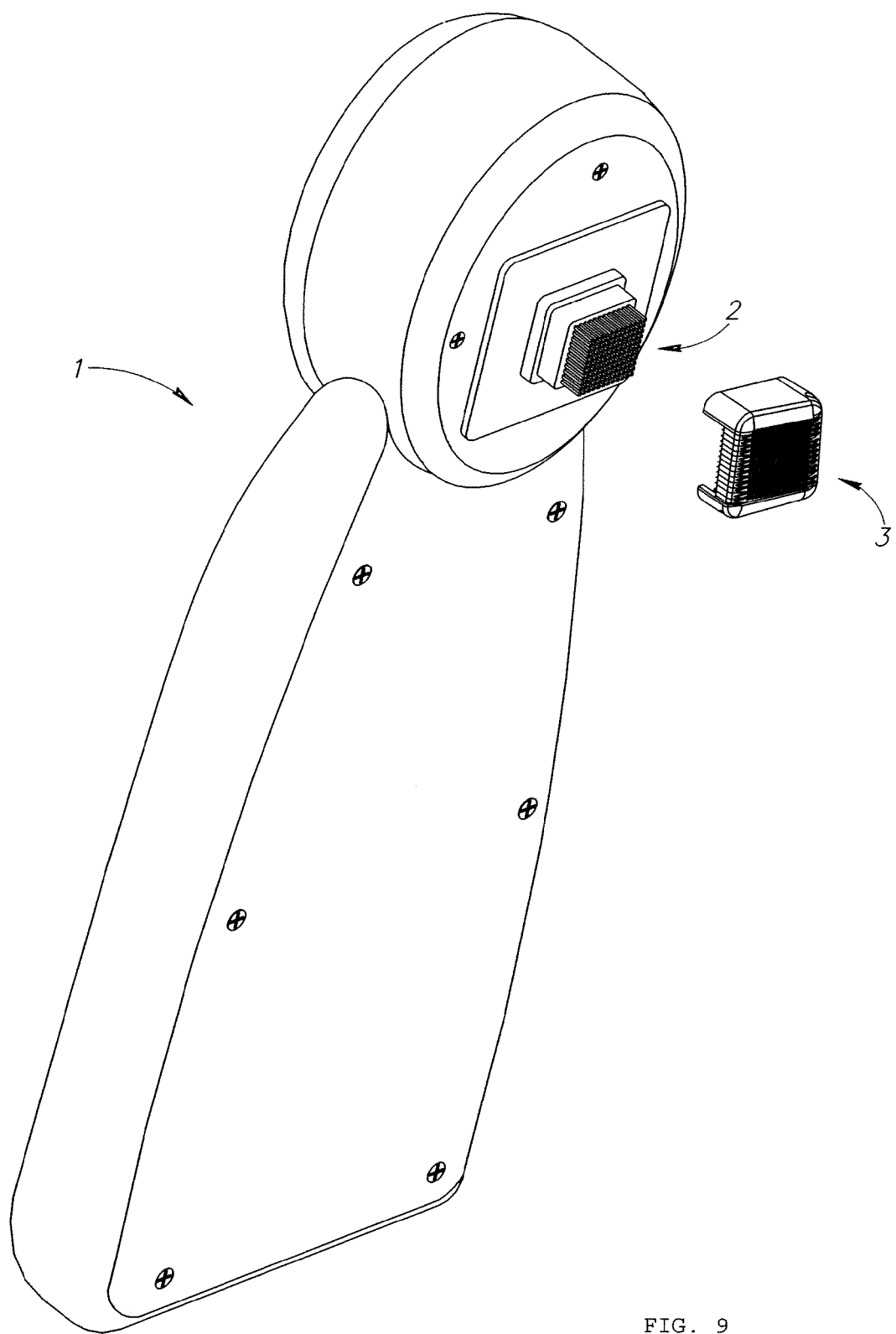
FIG. 9 shows the apparatus with the main unit (1) which contains electrical contacts (2) through which the electrical energy from the main unit is transferred to the electrode cartridge (3).
Figure 10:
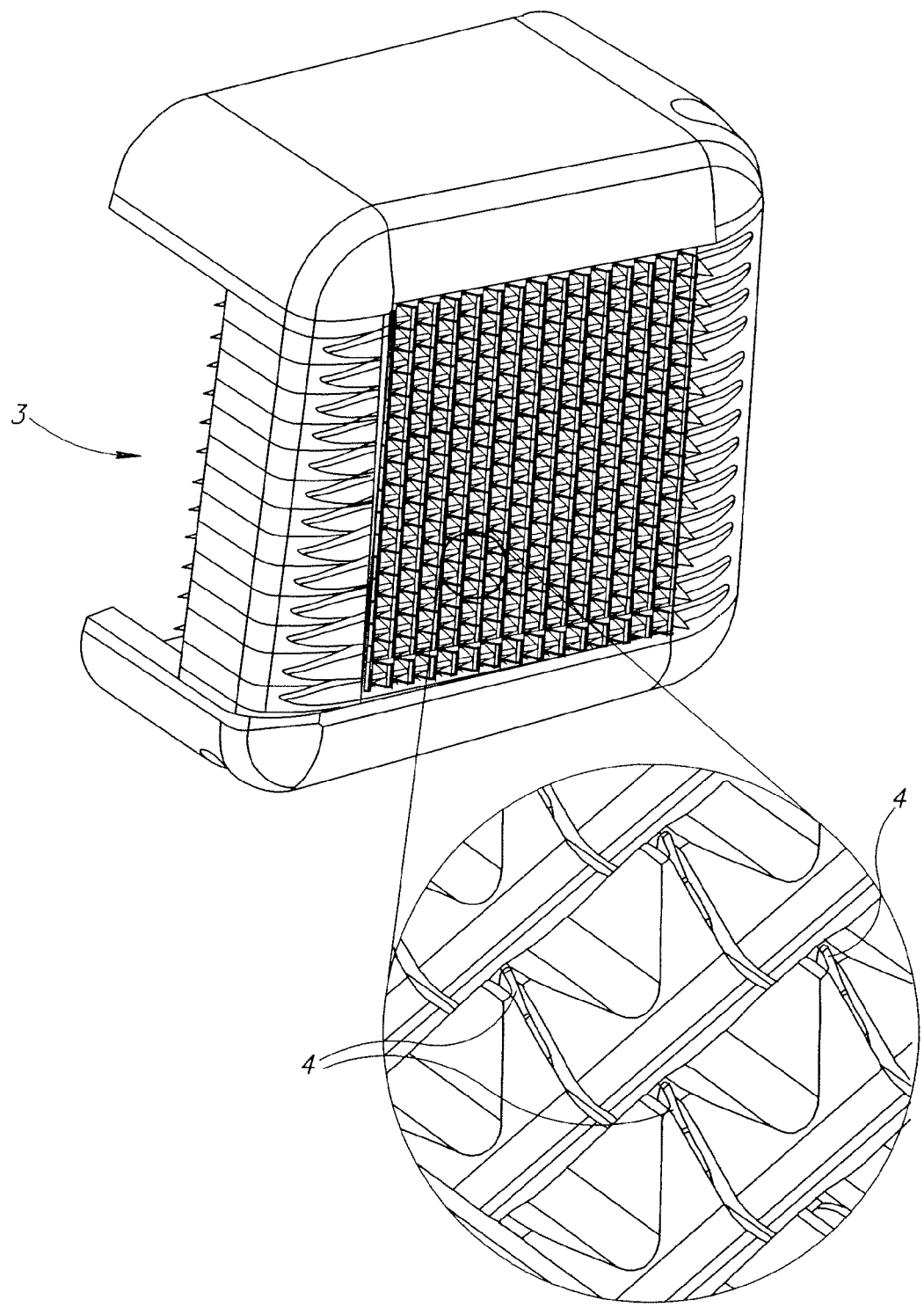
FIG. 10 is an enlarged view of a region of the electrode cartridge (3) showing the electrodes (4).

The biopotency of these treatments was assessed by determining glucose infusion rate (FIG. 8).

TABLE 8

Pharmacokinetic and pharmacodynamic in human subjects.

|  |  | ionto on + ViaDerm Part H | | ionto off + ViaDerm Part I | | SC-10U Part K | |
| --- | --- | --- | --- | --- | --- | --- | --- |
|  |  | mean | SD | mean | SD | mean | SD |
| Pharmacokinetic data | | | | | | | |
| Cmax | μU/ml | 83.0 | 23.5 | 27.0 | 8.3 | 17.8 | 6.3 |
| tmax | min | 199 | 33 | 217 | 75 | 214 | 111 |
| AUC | μU/ml/720 min | 24567 | 5695 | 8493 | 2801 | 5110 | 2453 |
| Total units delivered | | 48 | | 16.6 | | 10 | |
| Pharmacodynamic data | | | | | | | |
| GIRmax | mg/kg/min | 7.7 | 2.1 | 4.5 | 2.6 | 3.8 | 1.0 |
| tmax | min | 281 | 36 | 317 | 68 | 288 | 54 |
| AUC | mg/kg/720 min | 2736 | 781 | 1648 | 970 | 1541 | 350 |

Dermal Safety

The mean Primary Irritation Index scores of insulin (Humulin-500) delivery in the group treated with ViaDerm and iontophoresis up to 24 hours after patch removal indicated a "slight" potential for irritation effects immediately after patch removal (0.4<PII<1.9) and a "negligible" potential for irritation effects 24 hours after patch removal (0<PII<1.9), suggesting a transient irritation effect that decreased with time. The mean Primary Irritation Index scores for insulin (Humulin-500) delivery in the group treated with ViaDerm and then the iontophoresis patch was applied with no current supply indicated a "slight" potential for irritation effects immediately after patch removal (0.5<PII<1.9) and a "negligible" potential for irritation effects 24 hours post patch removal (0<PII<0.4), suggesting a transient irritation effect that decreased with time.

Conclusions

The application of the iontophoretic technology in combination with ViaDerm pretreatment using an iontophoretic gel patch enhances drug delivery by a factor of 3 in comparison to ViaDerm alone.

The amount of insulin delivered from an iontophoresis patch gel into skin treated with ViaDerm system (passive delivery) depends on the concentration of insulin. The amount of passive delivery of insulin Lispro 100 IU/ml was 4.3 units (Example 5 herein above) as compared to the amount of passive delivery of insulin R 500 IU/ml which was 16.6 units (Example 6).

Also, the amount of insulin delivered from an iontophoresis patch into skin treated with ViaDerm depends on the concentration of insulin. The amount of insulin Lispro 100 IU/ml delivered in the ViaDerm+iontophoresis group was 11 units (Example 5 herein above) as compared to the amount of insulin R 500 IU/ml delivered in the ViaDerm+iontophoresis group which was 48 units.

No delivery was observed using the iontophoretic technology alone.

Only slight Erythema and Edema was detected using the ViaDerm system, with and without application of the iontophoretic current.

It will be appreciated by persons skilled in the art that the present invention is not limited by what has been particularly shown and described herein above. Rather the scope of the invention is defined by the claims that follow.

What is claimed is:

1. A method for transdermal delivery of a pharmaceutical agent to a subject, which comprises:
   generating a plurality of micro-channels in a first region of the skin of a subject, wherein generating the plurality of micro-channels is performed by a micro-channel generating apparatus comprising: (i) an electrode cartridge comprising a plurality of electrodes; and (ii) a main unit comprising a control unit which is adapted to apply electrical energy between the plurality of electrodes of (i) when said plurality of electrodes are in vicinity of a first region of the skin, enabling ablation of stratum corneum in the first region of the skin beneath the plurality of electrodes, thereby generating a plurality of micro-channels;
   placing a first electrode assembly on said first region of the skin of the subject where the plurality of micro-channels are present, the first electrode assembly comprising a first electrode and an agent reservoir comprising a pharmaceutical agent, the agent reservoir being electrically connected to the first electrode;
   placing a second electrode assembly on a second region of the skin of the subject, the second electrode assembly comprising a second electrode and an electrolyte reservoir, with the first and second electrodes electrically connected to a power supply; and
   applying electric energy between the power supply and the first and second electrodes, thereby delivering iontophoretically the pharmaceutical agent through the plurality of micro-channels into the skin of the subject.

2. The method according to claim 1, wherein the electrodes having a diameter of about 30 microns to about 150 microns.

3. The method according to claim 2, wherein the electrodes having a diameter of about 40 microns to about 100 microns.

4. The method according to claim 3, wherein the electrodes having a diameter of about 80 microns.

5. The method according to claim 1, wherein the electrical energy is radio frequency energy.

6. The method according to claim 1, wherein the control unit generates current flow or one or more sparks.

7. The method according to claim 1, wherein the micro-channels have a density of about 75 to about 450 micro-channels/cm$^2$.

8. The method according to claim 7, wherein the micro-channels have a density of about 75 to about 300 micro-channels/cm$^2$.

9. The method according to claim 8, wherein the micro-channels have a density of about 150 micro-channels/cm$^2$.

10. The method according to claim 1, wherein the pharmaceutical agent is selected from the group consisting of anti-infectives, analgesics, anesthetics, antiarthritics, antiasthmatic agents, anticonvulsants, anti-depressants, anti-diabetic agents, anti-diarrhea agents, anti-histamines, anti-inflammatory agents, anti-migraine agents, anti-motion sickness preparations, anti-neoplastics, anti-parkinsonism drugs, anti-pruritics, anti-psychotics, antipyretics, anti-spasmodics, anticholinergics, sympathomimetics, xanthine derivatives, cardiovascular preparations, calcium channel blockers, beta-blockers, anti-arryhthmics, anti-hypertensives, diuretics, vasodilators, central nervous system stimulants, cough suppressants, cold suppressants, decongestants, diagnostics, hormones, hypnotics, immunosuppressives, muscle relaxants, parasympathomimetics, peptides, polypeptides, proteins, psychostimulants, sedatives and tranquilizers.

11. The method according to claim 10, wherein the pharmaceutical agent is a peptide, polypeptide or protein selected from the group consisting of insulin, proinsulin, follicle stimulating hormone, insulin like growth factor-1, insulin like growth factor-2, platelet derived growth factor, epidermal growth factor, fibroblast growth factors, nerve growth factor, transforming growth factors, tumor necrosis factor, calcitonin, parathyroid hormone, growth hormone, bone morphogenic protein, erythropoietin, hemopoietic growth factors, luteinizing hormone, calcitonin, glucagons, clotting factors, anti-clotting factors, bombesin, thrombin, enkephalinase, collagen, collagen domain, mullerian-inhibiting agent, relaxin A-chain, relaxin B-chain, prorelaxin, inhibin, activin, vascular endothelial growth factors, receptors for hormones, receptors for growth factors, integrin, protein A, protein D, rheumatoid factors, neurotrophic factors, CD proteins, osteoinductive factors, immunotoxins, interferons, colony stimulating factors, interleukins, superoxide dismutase, surface membrane proteins, decay accelerating factor, viral antigens, transport proteins; addressins, regulatory proteins, antibodies, and analogs, fragments and pharmaceutically acceptable salts thereof.

12. The method according to claim 11, wherein the pharmaceutical agent is selected from the group consisting of human insulin and human growth hormone.

13. The method according to claim 1, wherein the pharmaceutical agent reservoir further comprises at least one of the components selected from the group consisting of polymeric materials, electrolytes, preservatives, solubilizing agents, absorption promoters, and enzyme inhibitors.

* * * * *